(12) United States Patent
Kim et al.

(10) Patent No.: US 12,233,113 B2
(45) Date of Patent: Feb. 25, 2025

(54) PHARMACEUTICAL COMPOSITION COMPRISING RECOMBINANT HGH FOR THE TREATMENT OF GROWTH HORMONE DEFICIENCY

(71) Applicants: GENEXINE, INC., Gyeonggi-do (KR); HANDOK INC., Seoul (KR)

(72) Inventors: Tae Kyung Kim, Gyeonggi-do (KR); Young Joo Ahn, Gyeonggi-do (KR); Jung Won Woo, Seoul (KR); Ji-Eun Cha, Seoul (KR); Joan Yoon Ji Lee, Gyeonggi-do (KR); Woo Ick Jang, Seoul (KR)

(73) Assignees: GENEXINE, INC., Seongnam-si (KR); HANDOK INC., Seoul (KR)

( * ) Notice: Subject to any disclaimer, the term of this patent is extended or adjusted under 35 U.S.C. 154(b) by 1249 days.

(21) Appl. No.: 16/077,177

(22) PCT Filed: Feb. 16, 2017

(86) PCT No.: PCT/KR2017/001726
§ 371 (c)(1),
(2) Date: Aug. 10, 2018

(87) PCT Pub. No.: WO2017/142331
PCT Pub. Date: Aug. 24, 2017

(65) Prior Publication Data
US 2021/0177945 A1 Jun. 17, 2021

(30) Foreign Application Priority Data

Feb. 17, 2016 (KR) .................. 10-2016-0018695
Feb. 16, 2017 (KR) .................. 10-2017-0021104

(51) Int. Cl.
| | |
|---|---|
| A61K 38/16 | (2006.01) |
| A61K 9/00 | (2006.01) |
| A61K 38/18 | (2006.01) |
| A61K 38/22 | (2006.01) |
| A61K 38/27 | (2006.01) |
| A61P 5/06 | (2006.01) |
| C07K 14/61 | (2006.01) |

(52) U.S. Cl.
CPC ............ *A61K 38/27* (2013.01); *A61K 9/0019* (2013.01); *A61P 5/06* (2018.01)

(58) Field of Classification Search
CPC ........ A61K 38/27; A61K 9/0019; A61K 9/00; A61K 38/16; A61K 38/18; A61K 38/22; A61P 5/06; C07K 14/61; C07K 2319/30
See application file for complete search history.

(56) References Cited

U.S. PATENT DOCUMENTS

| | | | |
|---|---|---|---|
| 7,867,491 B2 | 1/2011 | Yang et al. | |
| 8,529,899 B2 | 9/2013 | Yang et al. | |
| 8,883,134 B2 | 11/2014 | Cho et al. | |
| 2010/0247608 A1 | 9/2010 | Azria et al. | |
| 2010/0261248 A1 | 10/2010 | Kim et al. | |
| 2012/0276097 A1 | 11/2012 | Yang et al. | |
| 2014/0162949 A1 | 6/2014 | Cleland et al. | |
| 2019/0224281 A1 | 7/2019 | Kim et al. | |

FOREIGN PATENT DOCUMENTS

| | | |
|---|---|---|
| CN | 102875683 A | 1/2013 |
| CN | 105209055 A | 12/2015 |
| KR | 1020080094781 A | 10/2008 |
| RU | 2009 111 391 | 10/2010 |
| WO | 2016/011281 | 1/2016 |
| WO | 2016/079302 A1 | 5/2016 |
| WO | 2018/044060 A1 | 3/2018 |

OTHER PUBLICATIONS

Pipelinereview.com, https://pipelinereview.com/index.php/2013082051798/Proteins-and-Peptides/Handok-Genexine-Long-Acting-hGH-Therapeutic-GX-H9-Receives-Approval-for-Phase-I-Trial-in-Europe.html, Aug. 20, 2013, pp. 1-2. (Year: 2013).*
Ku et al., "Long-acting FC-fusion rhGH (GX-H9) shows potential for u to twice-monthly administration in GH-deficient adults," European Journal of Endocrinology, 2018, 179, 169-179. (Year: 2018).*
"New therapeutic products for chronic hepatitis C patient", Journal of Clinical and Experimental Medicine, Vo. 225, No. 4, pp. 348-349, Apr. 26, 2008, 6 pages total.
Anonymous, "New Government Initiative for Drug Development—Korea Drug Development Fund", Jan. 1, 2013, pp. 1-20, XP055621921, 20 pages total.
Joan Lee, "GX-H9 (hGh-hyFc)", Genoxine, Inc., May 24, 2013, p. 1, XP055622171, 1 page total.
Jung-Won Woo et al., "LBFri-28: A Hybrid Fc-Fused Human Growth Hormone, GX-H9, Shows a Potential for Semi-Monthly Administration in Clinical Studies", Endocrine Society's 98th Annual Meeting and Expo, Apr. 1-4, 2016, Boston, XP055472540, 1 page total.
EunJig Lee et al., "A Hybrid Fc-fused Human Growth Hormone, GX-H9, Shows a Potential for Weekly and Semi-monthly Administration in Clinical Studies", ESPE2016, 55th Annual ESPE, vol. 86, RFC8.4, pp. 1-3, 2016, XP055622148, 3 pages total.
Anonymous,"KDDF-201308-07 Conduct and Completion of a Global Clinical Phase I Trial of a Next-Generation Human Growth Hormone Product(Metabolic Disorders,)", Korea Drug Development Fund, pp. 1-2, Jan. 12, 2016, XP055622221, 2 pages total.
Anonymous, "Development and Technology Transfer of Recombinant Human Growth Hormone Deficiency Therapeutics using Long-Acting Fc Fusion Protein Platform", Korea Drug Development Fund, pp. 1-3, XP055622234, 2016, 3 pages total.

(Continued)

*Primary Examiner* — Julie Ha
(74) *Attorney, Agent, or Firm* — Sughrue Mion, PLLC

(57) ABSTRACT

Provided are a method for administering a recombinant human growth hormone GX-H9 for treating growth hormone deficiency and a pharmaceutical composition containing a recombinant human growth hormone GX-H9 and a pharmaceutically acceptable carrier. The method includes administering recombinant human growth hormone GX-H9 once a week with a dosage of 0.1 to 0.3 mg per weight kg of a patient or twice-monthly with a dosage of 0.1 to 0.4 mg per weight kg of the patient.

4 Claims, 6 Drawing Sheets

Specification includes a Sequence Listing.

(56) References Cited

OTHER PUBLICATIONS

Anonymous, "Eu Clinical Trials Register", EudraCT No. 2015-001939-21, pp. 1-6, XP055622245, 2015, 6 pages total.
Anonymous, "Eu Clinical Trials Register", EudraCT No. 2014-002698-13, pp. 1-5, XP055622300, 2014, 5 pages total.
Russian Patent Office, Communication issued Jun. 14, 2019 in the copending Application No. 2018132694.
Handok-Genexine Long-Acting hGH Therapeutic "GX-H9" Receives Approval for Phase I Trial in Europe, retrieved Aug. 20, 2013, https://pipelinereview.com/index.php/2013082051798/Proteins-and-Peptides/Handok-Genexine-Long-Acting-hGH-Therapeutic-GX-H9-Receives-Approval-for-Phase-I-Trial-in-Europe.html.
Cook, D., et al., "Guidelines for Use of Growth Hormone in Clinical Practice", "Endocrine Practice", 2009, pp. 1-29, vol. 15, No. Suppl 2.
Cutfield, W., et al., "Non-Compliance With Growth Hormone Treatment in Children is Common and Impairs Linear Growth", "PLoS One", Jan. 2011, pp. 1-3, vol. 6, No. 1, e16223.
GH Research Society, "Consensus Guidelines for the Diagnosis and Treatment of Growth Hormone (GH) Deficiency in Childhood and Adolescence: Summary Statement of the GH Research Society", "Journal of Clinical Endocrinology & Metabolism", 2000, pp. 3990-3993, vol. 85, No. 11.
Hoybe, C., et al., "Status of Long-Acting-Growth Hormone Preparations—2015", "Growth Hormone & IGF Research", Jul. 2015, pp. 201-206, vol. 25.
Kim, E., et al., "Controlled Release of Human Growth Hormone Fused With a Human Hybrid Fc Fragment Through a Nanoporous Polymer Membrane", "Nanoscale", 2013, pp. 4262-4269, vol. 5.
Kim, S., et al., "Pharmacokinetics, Pharmacodynamics, and Efficacy of a Novel Long-Acting Human Growth Hormone: Fc Fusion Protein", "Molecular Pharmaceutics", Sep. 15, 2015, pp. 3759-3765, vol. 12.
Rosenfeld, R., et al., "Compliance and Persistence in Pediatric and Adult Patients Receiving Growth Hormone Therapy", "Endocrine Practice", Mar. 2008, pp. 143-154, vol. 14, No. 2.
National Digital Science Library, "Conduct Phase 1 Study in EU for Next Generation Human Growth Hormone (GX-H9)", "National Digital Science Library", Jun. 2014, pp. 1-48.
National Digital Science Library, "Conduct Phase 1 Study in EU for Next Generation Human Growth Hormone (GX-H9)", "National Digital Science Library", Jun. 2014, Page(s) English Abstract.
International Search Report dated Nov. 20, 2017 in International Application No. PCT/KR2017/009471.
Written Opinion of the International Searching Authority dated Nov. 20, 2017 in International Application No. PCT/KR2017/009471.
Charlotte Hoybye et al., "Status of long-acting-growth hormone preparations", Growth Hormone & IGF Research, 2015, vol. 25, pp. 201-206 (6 pages total).
Eung-Sam Kim et al., "Controlled release of human growth hormone fused with a human hybrid Fc fragment through a nanoporous polymer membrane", Nanoscale, 2013, vol. 5, pp. 4262-4269 (8 pages total).
Jeffrey L. Cleland et al., "A Novel Long-Acting Human Growth Hormone Fusion Protein (VRS-317): Enhanced in Vivo Potency and Half-Life", Journal of Pharmaceutical Sciences, 2012, vol. 101, No. 8, pp. 2744-2754 (11 pages total).
Su Jin Kim et al., "Pharmacokinetics, Pharmacodynamics, and Efficacy of a Novel Long-Acting Human Growth Hormone: Fc Fusion Protein", Molecular Pharmaceutics, 2015, vol. 12, pp. 3759-3765 (7 pages total).
W.M. Drake et al., "Optimizing Growth Hormone Replacement Therapy by Dose Titration in Hypopituitary Adults", Journal of Clinical Endocrinology and Metabolism, 1998, vol. 83, No. 11, pp. 3913-3919 (7 pages total).
William R. Strohl, "Fusion Proteins for Half-Life Extension of Biologics as a Strategy to Make Biobetters", BioDrugs, 2015, vol. 29, pp. 215-239 (25 pages total).
International Search Report dated May 17, 2017 in International Application No. PCT/KR2017/001726.
Written Opinion of the International Searching Authority dated May 17, 2017 in International Application No. PCT/KR2017/001726.
Vishakha V. Ambardekar et al., "NBCD Pharmacokinetics and Bioanalytical Methods to Measure Drug Release", AAPS Advances in the Pharmaceutical Sciences Series, 2015, pp. 261-287 (27 pages).
EUDRACT No. 2014-0026998-13, "A randomized, active-controlled, multiple-dose, open-label study to evaluate the safety, tolerability, and efficacy of the long-acting antibody-fused recombinant human growth hormone (GX-H9) in adult growth hormone deficiency (AGHD)", URL: https://www.clinicaltrialsregister.eu/ctr-search/trial/2014-002698-13/PL, 2014, 8 pages.

* cited by examiner

SEQUENCE LISTING

```
<160> NUMBER OF SEQ ID NOS: 1

<210> SEQ ID NO 1
<211> LENGTH: 436
<212> TYPE: PRT
<213> ORGANISM: Artificial Sequence
<220> FEATURE:
<223> OTHER INFORMATION: GX-H9

<400> SEQUENCE: 1

Phe Pro Thr Ile Pro Leu Ser Arg Leu Phe Asp Asn Ala Met Leu Arg
1               5                   10                  15

Ala His Arg Leu His Gln Leu Ala Phe Asp Thr Tyr Gln Glu Phe Glu
            20                  25                  30

Glu Ala Tyr Ile Pro Lys Glu Gln Lys Tyr Ser Phe Leu Gln Asn Pro
        35                  40                  45

Gln Thr Ser Leu Cys Phe Ser Glu Ser Ile Pro Thr Pro Ser Asn Arg
    50                  55                  60

Glu Glu Thr Gln Gln Lys Ser Asn Leu Glu Leu Leu Arg Ile Ser Leu
65                  70                  75                  80

Leu Leu Ile Gln Ser Trp Leu Glu Pro Val Gln Phe Leu Arg Ser Val
                85                  90                  95

Phe Ala Asn Ser Leu Val Tyr Gly Ala Ser Asp Ser Asn Val Tyr Asp
            100                 105                 110

Leu Leu Lys Asp Leu Glu Glu Gly Ile Gln Thr Leu Met Gly Arg Leu
        115                 120                 125

Glu Asp Gly Ser Pro Arg Thr Gly Gln Ile Phe Lys Gln Thr Tyr Ser
    130                 135                 140

Lys Phe Asp Thr Asn Ser His Asn Asp Asp Ala Leu Leu Lys Asn Tyr
145                 150                 155                 160

Gly Leu Leu Tyr Cys Phe Arg Lys Asp Met Asp Lys Val Glu Thr Phe
                165                 170                 175

Leu Arg Ile Val Gln Cys Arg Ser Val Glu Gly Ser Cys Gly Phe Arg
            180                 185                 190

Asn Thr Gly Arg Gly Gly Glu Glu Lys Lys Glu Lys Glu Lys Glu
        195                 200                 205

Glu Gln Glu Glu Arg Glu Thr Lys Thr Pro Glu Cys Pro Ser His Thr
    210                 215                 220

Gln Pro Leu Gly Val Phe Leu Phe Pro Pro Lys Pro Lys Asp Thr Leu
225                 230                 235                 240

Met Ile Ser Arg Thr Pro Glu Val Thr Cys Val Val Val Asp Val Ser
                245                 250                 255

Gln Glu Asp Pro Glu Val Gln Phe Asn Trp Tyr Val Asp Gly Val Glu
            260                 265                 270

Val His Asn Ala Lys Thr Lys Pro Arg Glu Glu Gln Phe Asn Ser Thr
        275                 280                 285

Tyr Arg Val Val Ser Val Leu Thr Val Leu His Gln Asp Trp Leu Asn
    290                 295                 300

Gly Lys Glu Tyr Lys Cys Lys Val Ser Asn Lys Gly Leu Pro Ser Ser
305                 310                 315                 320

Ile Glu Lys Thr Ile Ser Lys Ala Lys Gly Gln Pro Arg Glu Pro Gln
                325                 330                 335
```

```
Val Tyr Thr Leu Pro Pro Ser Gln Glu Glu Met Thr Lys Asn Gln Val
            340             345                 350

Ser Leu Thr Cys Leu Val Lys Gly Phe Tyr Pro Ser Asp Ile Ala Val
            355             360             365

Glu Trp Glu Ser Asn Gly Gln Pro Glu Asn Asn Tyr Lys Thr Thr Pro
    370             375             380

Pro Val Leu Asp Ser Asp Gly Ser Phe Phe Leu Tyr Ser Arg Leu Thr
385             390             395                         400

Val Asp Lys Ser Arg Trp Gln Glu Gly Asn Val Phe Ser Cys Ser Val
            405             410             415

Met His Glu Ala Leu His Asn His Tyr Thr Gln Lys Ser Leu Ser Leu
            420             425             430

Ser Leu Gly Lys
        435
```

PHARMACEUTICAL COMPOSITION COMPRISING RECOMBINANT HGH FOR THE TREATMENT OF GROWTH HORMONE DEFICIENCY

CROSS-REFERENCE TO RELATED APPLICATIONS

This is a U.S. national phase under the provisions of 35 U.S.C. § 371 of International Patent Application No. PCT/KR17/01726 filed Feb. 16, 2017, which in turn claims priority of Korean Patent Application No. 10-2016-0018695filed Feb. 17, 2016 and Korean Patent Application No. 10-2017-0021104 filed Feb. 16, 2017. The disclosures of International Patent Application No. PCT/KR17/01726, Korean Patent Application No. 10-2016-0018695, and Korean Patent Application No. 10-2017-0021104 are hereby incorporated herein by reference in their respective entireties, for all purposes.

TECHNICAL FIELD

The present disclosure relates to a pharmaceutical composition for treating growth hormone deficiency, containing hGH-hyFc (GX-H9) which is a recombinant human growth hormone prepared by fusing hybrid Fc to human growth hormone hGH. More particularly, the present disclosure relates to a appropriate method of administering a recombinant hGH which is effective to treat the growth hormone deficiency and to a pharmaceutical composition for treating growth hormone deficiency, including a recombinant hGH GX-H9 and a pharmaceutically acceptable carrier, in which the recombinant hGH GX-H9 is administered once a week with a dosage of 0.1 to 0.3 mg per weight kg of a patient or twice-monthly with a dosage of 0.1 to 0.4 mg per weight kg of the patient. Further, the present disclosure relates to a method for treating growth hormone deficiency, including administering an recombinant hGH GX-H9 to a patient with growth hormone deficiency once a week with a dosage of 0.1 to 0.3 mg per weight kg of the patient or twice-monthly with a dosage of 0.1 to 0.4 mg per weight kg of the patient.

BACKGROUND ART

Growth hormone is a hormone which is secreted from an anterior pituitary gland, as a single molecular polypeptide composed of 191 amino acids. Insulin like growth factor-1 (IGF-1) is expressed in combination with a growth hormone receptor to be involved in growth and regeneration of cells. It is known that the growth hormone is produced in the pituitary gland of the normal human body, and gradually increased until adolescence and gradually decreased with age.

The most common growth hormone deficiency is adult growth hormone deficiency (AGHD) and pediatric growth hormone deficiency (PGHD). The adult growth hormone deficiency occurs when the patient's pituitary gland is injured by radiation or surgery in the treatment of brain tumors and cerebral hemorrhage, or idiopathically. If the secretion of the growth hormone is not performed well, symptoms including a loss in weight, reduction of the mineral density of the bone, increase in the fat, reduction of HDL, increase of LDL, decrease in muscle strength, and the like are shown, and thus, life quality is deteriorated. In adult patients with growth hormone deficiency, the concentration of IGF-1 in serum belongs to a standard deviation score (SDS) of −2 or less (<−2 SDS) or within 2.5 percentile (<2.5 percentile) as compared with normal people in the same age group. The response value of the growth hormone in the blood may be measured by stimulation tests such as an insulin tolerance test (ITT), an arginine load test (GHRH+ARG), a glucagon test, an L-DOPA test and a clonidine test. When the peak GH of the growth hormone is 11.0 µg/L or less in patients with a body mass index (BMI) of less than 25 kg/m$^2$, 8.0 µg/L or less in patients with a BMI of 25 to 30 kg/m$^2$, or 4.0 µg/L or less in patients with a BMI of more than 30 kg/m$^2$, the peak GH is considered as deficiency (Guidelines for Use of Growth Hormone in Clinical Practice, *Endocr. Pract.* 2009; 15 (Suppl 2)).

Pediatric growth hormone deficiency occurs when damage of the pituitary gland or developmental disorders is present. A growth hormone secretion disorder is shown as short stature, and height with growth lower 3% or 5 cm or less a year in the growth curve of the same age, and symptoms such as hypoglycemia, deterioration of stamina, depression, and mental immaturity may be shown. In the case where the height is lower than the mean by 3 SD or more at the same age, in the case where the height is lower than the average of the parent's height by 1.5 SD or more, in the case where the height is lower than the mean height by 2 SD or more and lower than the same age growth by 1 SD or more for 1 year or more, in the case where the height is lower than the same age growth by 0.5 SD or more for 2 years or more, or in the case where although the low growth symptoms are not shown, the height is maintained at less than 2 SD for 1 year or more or 1.5 SD for 2 years or more, the symptom may be determined as pediatric growth hormone deficiency (Consensus guideline for the diagnosis and treatment of GH deficiency in childhood and adolescence: summary statement of the GH Research Society. GH Research Society, *J. Clin. Endocrinol. Metab.*, 2000 November; 85(11): 3990-3).

In the case of adult growth hormone deficiency, the dosage of the drug was selected on the basis of the weight of the patient in the related art, but recently, the patient is treated with the individualized dosage. That is, the treatment starts at a dosage lower than an expected therapeutic optimum dosage and adjusted by a method of increasing or decreasing 0.1 to 0.2 mg/day dosage depending on clinical response, adverse events (fasting glucose), or a IGF-1 level. Gender, estrogen status, and age of the patient need to be considered when selecting the treatment dosage of the growth hormone. The goal of treatment in patients with adult growth hormone deficiency is to improve metabolism normalization and quality of life. To this end, the IGF-1 level in the blood needs to be optimized to the middle (50th percentile or 0 SDS) to 1 SDS of the normal range (−2 SDS to 2 SDS) of dosage according to age and gender.

In the case of the pediatric growth hormone deficiency, it is recommended that treatment starts as soon as possible after being diagnosed as a patient. Generally, a method of subcutaneous administration of growth hormone every night is used and the recommended dosage is 25 to 50 µg/kg/day. Typically, the growth rate is checked periodically at 3 months or 6 months and it is recommended to verify adverse events for verifying height growth, a change in growth rate, patient's individual compliance, and safety, and to verify IGF-1 or IGFBP-3 levels in the serum. A treatment goal in patients with pediatric growth hormone deficiency is to normally grow the height and growth hormone needs to be administered so that the IGF-1 levels in the blood are close to the average of same age (50th percentile or 0 SDS).

Growth hormone is extracted from the pituitary gland of dead body when the growth hormone treatment starts for the first time in the 1950s, and the supply is very limited and the cost is expensive because the amount of growth hormone extracted from one person is very small. With development of gene recombinant technologies, growth hormone synthesized in *Escherichia coli* was released (Somatropin, 1981, Genentech Corporation in USA). The recombinant growth hormone drugs currently marketed in the USA include Genotropin by Pfizer, Humatrope by Eli Lilly, Nutropin by Genentech, Norditropin by Novo Nordisk, and the like.

However, the recombinant growth hormone preparations are daily formulations requiring administration 6 times or 7 times a week. In adult growth hormone deficiency, Humatrope is used with a dosage of 0.2 mg/day (a range of 0.15 to 0.30 mg/day). When Nutropin is not based on body weight and set as a dosage, the starting dosage is 0.2 mg/day (a range of 0.15 to 0.3 mg/day) and can be changed to a dosage of 0.1 to 0.2 mg/day in 1 to 2 month cycles. When the dosage of Nutropin is set based on the body weight, the starting dosage is used so as not to exceed 0.005 mg/kg/day or more. If it is necessary to increase the dosage, the dosage is increased so as not to exceed 0.01 mg/kg/day after 4 weeks of administration. When Norditropin is not based on body weight and set as a dosage, the starting dosage is 0.2 mg/day (a range of 0.15 to 0.3 mg/day) and can be changed to a dosage of 0.1 and 0.2 mg/day in 1 to 2 month cycles. When the dosage of Norditropin is set based on the body weight, the starting dosage is used so as not to exceed 0.004 mg/kg/day or more. If it is necessary to increase the dosage, the dosage is increased so as not to exceed 0.016 mg/kg/day or more after 6 weeks of administration. In the case of pediatric growth hormone deficiency, Genotropin is used with a dosage of 0.16 to 0.24 mg/kg/week and Humatrope is used with a dosage of 0.026 to 0.043 mg/kg/day. Nutropin is used with a dosage of 0.3 mg/kg/week and Norditropin is used with a dosage of 0.024 to 0.034 mg/kg/day.

Currently, growth hormone preparations are one-day formulations, and particularly, in the case of pediatric patients, it is inconvenient to inject the drug every day for a long treatment period of 3 to 4 years, and it is known that the mental stress caused by injection reduces the quality of life of the patient. In addition, dosing compliance of frequency by patient becomes the biggest factor that hinders the treatment effect. Further, it is also known that the number of administration failures increases markedly as increasing treatment duration (*Endocrine practice*, 2008 March; 14 (2): 143-54). Approximately 2/3 of patients have low compliance according a default, and actually, it is known to reduce a height growth speed (*PloS one*, 2011 January; 6(1): e16223).

Due to these problems, attempts to develop long-acting growth hormone have been made by using various techniques, but until now, the development is successful and as a product released in the market, one long-acting formulation is unique. Nutropin depot was developed by Genentech in the US as a monthly formulation, but due to is difficulty of production, it was withdrawn from the market. Eutropin Plus/Declage by LG Life Sciences developed a weekly formulation using hyaluronic acid (HA), but due to needle larger needle size compared to first generation, it contains inconvenience.

Therefore, it is necessary to develop safe and effective long-acting growth hormone while satisfying the convenience of the patient due to reduced compliance. GX-H9 (hGH-hybrid Fc) is a long-acting growth hormone preparation under clinical development. In U.S. Pat. No. 7,867,491, a hybrid type Fc capable of overcoming complement dependent cytotoxicity and antibody dependent cellular cytotoxicity which are problems of the existing Fc fusion technology was prepared by combining immunoglobulin IgD and immunoglobulin IgG4. Subsequently, in U.S. Pat. No. 8,529,899, a recombinant hGH (hGH-hyFc, GX-H9) which is a material capable of replacing an existing daily-type growth hormone formulation was prepared by fusing hybrid Fc to human growth hormone hGH. However, the actual half-life in the body and therapeutic dosage of the Fc fused protein is greatly changed depending on what kind of pharmacologically active ingredient is bound to Fc. The effective and safe dosages and its frequency for the treatment of growth hormone deficiency using GX-H9, in which human growth hormone hGH is fused to hyFc, have not yet been found.

Therefore, in the present disclosure, clinical trials targeting 32 healthy adults (2013-002771-18) and 45 adult patients with growth hormone deficiency (2014-002698-13), EudraCT) was conducted to develop dosage and dose frequency showing the optimal effect of recombinant growth hormone, GX-H9. As a result, the present disclosure was completed by confirming dosage, dose frequency and safety of GX-H9 that is maintains the IGF-1 SDS value in normal range with minimum number of side effects caused by growth.

DISCLOSURE

Technical Problem

An object of the present disclosure is to providing a method for treating growth hormone deficiency comprising administering recombinant hGH, GX-H9, to a patient with growth hormone deficiency once with an interval of at least a week and with a dosage of at least 0.1 mg per weight kg of a patient.

An object of the present disclosure is to providing a method for treating growth hormone deficiency using an recombinant hGH GX-H9 by determining a dosage and a dose frequency of the recombinant hGH GX-H9 which is effective to treat the growth hormone deficiency.

An aspect of the present disclosure provides a pharmaceutical composition for treating growth hormone deficiency comprising a recombinant human growth hormone, GX-H9, and a pharmaceutically acceptable carrier, wherein the recombinant hGH is administered once with an interval of at least a week and with a dosage of at least 0.1 mg per weight kg of a patient.

Technical Solution

An aspect of the present disclosure provides a pharmaceutical composition for treating growth hormone deficiency comprising a recombinant human growth hormone, GX-H9, and a pharmaceutically acceptable carrier, in which the recombinant hGH is administered once a week with a dosage of 0.1 to 0.3 mg per weight kg of a patient.

Another aspect of the present disclosure provides a pharmaceutical composition for treating growth hormone deficiency comprising an recombinant hGH GX-H9 and a pharmaceutically acceptable carrier, in which the recombinant hGH is administered twice-monthly with a dosage of 0.1 to 0.4 mg per weight kg of a patient.

Yet another aspect of the present disclosure provides a method for treating growth hormone deficiency including administering recombinant human growth hormone, GX-H9, to a patient with growth hormone deficiency once a week with a dosage of 0.1 to 0.3 mg per weight kg of the patient.

Still another aspect of the present disclosure provides a method for treating growth hormone deficiency including administering a recombinant human growth hormone, GX-H9, to a patient with growth hormone deficiency twice-monthly with a dosage of 0.1 to 0.4 mg per weight kg of the patient.

According to the present disclosure, when the recombinant human growth hormone, GX-H9, is administered to a patient with growth hormone deficiency once a week with a dosage of 0.1 to 0.3 mg per weight kg of the patient or twice-monthly with a dosage of 0.1 to 0.4 mg per weight kg of the patient, the level of growth hormone in the body can be maintained for a longer period and in respect to hGH level, IGF-1 SDS value may be maintained in normal range for longer time. Thus, giving possibility to treat growth hormone deficiency by administering a growth hormone once a week or twice-monthly without the need for daily administration.

DESCRIPTION OF DRAWINGS

The above and other aspects, features and other advantages of the present disclosure will be more clearly understood from the following detailed description taken in conjunction with the accompanying drawings, in which.

MODE FOR INVENTION

Figure 1:
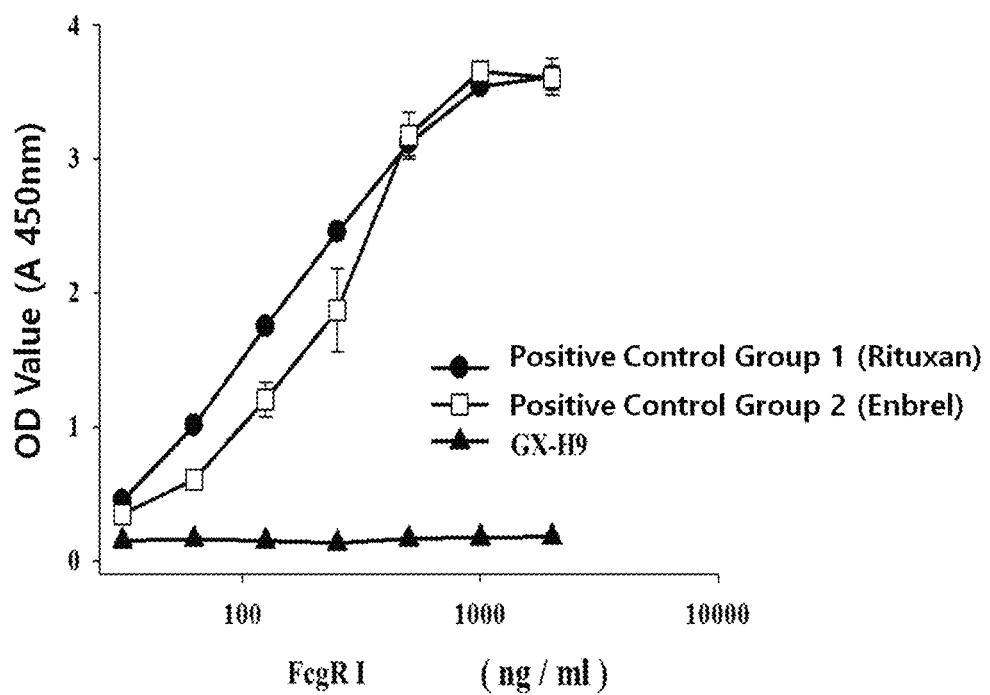
FIG. 1 illustrates a result of binding affinity of a Fcγ receptor FcγR I for the recombinant hGH (GX-H9)

Effective dosage and dose frequency of recombinant human growth hormone GX-H9 that promotes actual growth in the human are not yet found.

The inventors conducted clinical studies in order to develop the dosage and the dose frequency capable of exhibiting an optimal effect of GX-H9, by targeting 32 healthy adults (2013-002771-18) and 45 adult patients with growth hormone deficiency (2014-002698-13, EudraCT). As a result, it has been observed that in the case of administering the recombinant hGH, GX-H9, once a week with a dosage of 0.1 to 0.3 mg per weight kg of the patient or twice-monthly with a dosage of 0.1 to 0.4 mg per weight kg of the patient, the growth hormone in the body is maintained for a longer period and the IGF-1 SDS value may be maintained in normal range.

One aspect of the present disclosure relates to pharmaceutical composition for treating growth hormone deficiency containing a recombinant hGH (GX-H9) and a pharmaceutically acceptable carrier, wherein the recombinant hGH is administered once with an interval of at least a week and with a dosage of at least 0.1 mg per weight kg of a patient.

One aspect of the present disclosure relates to pharmaceutical composition for treating growth hormone deficiency containing a recombinant hGH (GX-H9) and a pharmaceutically acceptable carrier, in which the recombinant hGH is administered once a week with a dosage of 0.1 to 0.3 mg per weight kg of a patient. Particularly, the present disclosure relates to a pharmaceutical composition, in which the recombinant hGH is administered once a week with a dosage of 0.1 to 0.2 mg per weight kg of a patient.

Further, another aspect of the present disclosure relates to a pharmaceutical composition for treating growth hormone deficiency containing an recombinant hGH protein GX-H9 and a pharmaceutically acceptable carrier, in which the recombinant hGH is administered twice-monthly with a dosage of 0.1 to 0.4 mg per weight kg of a patient. Particularly, the present disclosure relates to a pharmaceutical composition, in which the recombinant hGH is administered once two weeks with a dosage of 0.15 to 0.4 mg per weight kg of a patient.

In the pharmaceutical composition of the present disclosure, the recombinant hGH, GX-H9, may include an amino acid sequence of SEQ ID NO: 1. The pharmaceutical composition of the present disclosure may be administered subcutaneously.

Further, yet another aspect of the present disclosure provides a method for treating patients with growth hormone deficiency comprising administering an recombinant hGH GX-H9 to a patient with growth hormone deficiency once a week with a dosage of 0.1 to 0.3 mg per weight kg of the patient.

Further, still another aspect of the present disclosure provides a method for treating patients with growth hormone deficiency comprising administering an recombinant hGH GX-H9 to a patient with growth hormone deficiency twice-monthly with a dosage of 0.1 to 0.4 mg per weight kg of the patient.

The recombinant hGH "GX-H9" used in the present application is referred to as hGH-hyFc which is a human growth hormone fused to hybrid Fc and may have an amino acid sequence of SEQ ID NO: 1. The recombinant hGH GX-H9 may be prepared by a method disclosed in U.S. Pat. No. 8,529,899.

According to the present disclosure, the pharmaceutical composition containing the recombinant hGH GX-H9 may be administered to adults with growth hormone deficiency. The adult growth hormone deficiency means a case where a standard deviation score (SDS) compared to normal people in the same age group in adults is −2 or less (<−2 SDS) or within 2.5 percentile (<2.5 percentile). In adults with pituitary diseases and hypopituitarism, the grown hormone deficiency is usually involved with physical and could cause mental disorders as well as body composition and metabolic abnormalities. The adult grown hormone deficiency may be classified into three categories. The adult grown hormone deficiency may be divided into first, childhood-onset growth hormone deficiency, case of grown hormone deficiency due to hypothalamic-pituitary-based disorders, and idiopathic grown hormone deficiency.

The pharmaceutical composition of the present disclosure may include a pharmaceutically acceptable carrier that may be any non-toxic material suitable for delivering the recombinant hGH to the patient. Distilled water, alcohol, fats, waxes and inert solids may be included as the carrier. Pharmaceutically acceptable adjuvants such as a buffer, a dispersant, and a diluent, for example, bacteriostatic water for injection (BWFI), phosphate buffered saline, a ringer's solution, a dextrose solution, sucrose, poloxamer, and the like may be included in the pharmaceutical composition of the present disclosure.

In the present disclosure, the recombinant hGH, GX-H9, may be administered once a week with a dosage of 0.1 to 0.3 mg per weight kg of the patient and for example, the administrative dose may vary with dosage of 0.1, 0.15, 0.2, 0.25, or 0.3 mg per weight kg according to age, gender, and estrogen states of patients. Preferably, the recombinant hGH GX-H9 may be administered once a week with a dosage of 0.1 to 0.2 mg per weight kg of the patient. Further, the recombinant hGH GX-H9 may be administered twice-monthly with a dosage of 0.1 to 0.4 mg per weight kg of the patient and for example, may be administered once two weeks with a dosage of 0.1, 0.15, 0.2, 0.25, 0.3, 0.35, or 0.4 mg per weight kg of the patient according to age, gender, and estrogen states. Preferably, the recombinant hGH GX-H9 may be administered twice-monthly with a dosage of 0.15 to 0.4 mg per weight kg of the patient. Particularly, the preferred dosage of the recombinant hGH, GX-H9, is 0.1 mg/kg administered once a week, 0.2 mg/kg administered twice-monthly, or 0.3 mg/kg administered twice-monthly. Further, in some cases, the recombinant hGH may be administered twice-monthly, once in three weeks, or monthly with 0.3 to 0.6 mg/kg according to the age, gender, and estrogen states.

The dosage of the recombinant hGH may be adjusted based on the age, gender, and estrogen state of the patient and may be increased or decreased while monitoring the progress of administration. The dosage of the recombinant hGH administered subsequently may be higher or lower than an initial dosage or equal to the initial dosage as level of IGF-1 SDS changes. At the initial stage, a small amount of recombinant hGH should be administered safely and then may gradually be increased after verifying no adverse reaction. Further, the dosage of the recombinant hGH may be adjusted while the level of IGF-1 SDS in change is monitored in a plasma or serum sample of the patient. The dosage of the recombinant hGH suitable for each individual patient may vary depending on age, gender, constitution, body weight of the patient.

The pharmaceutical composition of the present disclosure containing the recombinant hGH, GX-H9, may be administered to a subject by various methods. For example, the pharmaceutical composition may be administered parenterally and for example, subcutaneously, intramuscularly or intravenously. The composition may be sterilized according to a generally well-known sterilization technique. The composition may include pharmaceutically acceptable auxiliary substances and adjuvants, toxic modifiers and analogs thereof required for adjusting physiological conditions such as pH adjustment, and for example, may include sodium acetate, sodium chloride, potassium chloride, calcium chloride, sodium lactate, and the like. In the formulations, the concentration of the recombinant hGH may be very various and may be selected preferentially based on a body fluid volume, viscosities, and the like according to the selected specific administration method.

Hereinafter, the present disclosure will be described in more detail through Examples. These Examples are just to exemplify the present disclosure, and it is apparent to those skilled in the art that it is interpreted that the scope of the present disclosure is not limited to these Examples.

Example 1. Preparation of Recombinant hGH, GX-H9

The recombinant hGH, GX-H9, may be prepared according to a method disclosed in U.S. Pat. No. 8,529,899.

First, a nucleic acid sequence of hGH-hyFc in which hyFc was fused to human growth hormone (hGH) encoding an amino acid sequence of SEQ ID NO: 1 was inserted to an expression vector pAD15 to produce cell line expressing hGH-hyFc. To produce a vector including a hGH-hyFc structural gene, GenBank AAA98618.1 sequence was used for human growth hormone hGH gene and a gene of hyFc was produced by fusing GenBank P01880 (IgD) and GenBank AAH25985 (IgG4) sequences. Genes obtained through gene manufacturer were injected by using specific restriction enzymes as expression vectors for preparation of cell line production.

The expression vector ensured by the method above was transfected into CHO DG44 (Columbia University, USA) cells by a calcium phosphate method. After 6 hrs of the transfection, the transfected cells were washed with a phosphate buffer and then a medium was replaced with 10% dFBS (Gibco, USA, 30067-334), MEM alpha (Gibco, 12561, USA, Cat No. 12561-049), and HT+ (Gibco, USA, 11067-030) media. After 48 hrs of the transfection, HT selection was performed by continuously diluting the transfected cells in a 100 mm plate using a 10% dFBS+MEM alpha medium without HT. While the medium was replaced twice a week, the transfected cells were left until a single colony was formed. Thereafter, in order to amplify productivity using a DHFR-system, MTX amplification was performed with respect to clones from HT selection. After the MTX amplification, 4 to 5 times of sub-culture was performed to stabilize the cell for the productivity evaluation and the unit productivity was evaluated. A clone suitable for producing a target protein was obtained.

To obtain the single clone with respect to the most productive clones, limiting dilution cloning (LDC) was performed. The LDC was inoculated in a 96-well plate by diluting the cells with a culture medium to have a concentration of 1 cell/well. After 10 to 14 days of inoculation, only cells of wells with single clones were obtained through a microscope and cultured in a T25 flask enough to perform productivity evaluation, and then a cell line having high productivity was ensured.

After a culture solution was obtained from the ensured cell line, target protein was purified from the culture solution. A protein culture solution sample went through sample binding using the protein culture solution using Prosep® Ultra Plus (Merck) and was equilibrated by using 50 mM sodium phosphate, 150 mM sodium chloride and a pH 7.0 buffer. XK16/20 column (GE Healthcare) was used and the protein was eluted by using 100 mM sodium citrate, 200 mM L-arginine and pH 3.1 buffer.

Example 2. Antibody-Dependent Cell-Mediated Cytotoxicity (ADCC) and Complement-Mediated Cytotoxicity (CDC) Tests of Recombinant hGH GX-H9

To verify that a hybrid Fc domain of GX-H9 did not induce antibody dependent cell mediated cytotoxicity (ADCC) and complement dependent cytotoxicity (CDC), an enzyme-linked immunosorbent assay (ELISA) was performed.

As positive control groups, Rituxan (by Roche Corporation in Switzerland) and Enbrel (by Amgen Corporation in USA), which were known to have very high binding affinity to Fcγ receptors FcγR I, II and III, were used. GX-H9, Rituxan, and Enbrel were coated on each 96-well plate and then reacted with the Fcγ receptor I with serial dilution. After the reaction time elapsed, the reaction solution was washed with a buffer solution to remove the Fcγ receptor I that was not bound to test substances. Thereafter, binding force between the Fcγ receptor I and the test substance was measured by using a biotinylated anti-FcγRI antibody and an HRP conjugated streptavidin antibody.

Binding force between C1q and GX-H9 inducing cell-mediated cytotoxicity was also measured by using the above ELISA method. As positive control groups, Rituxan (by Roche Corporation in Switzerland) and Enbrel (by Amgen Corporation in USA) was used and binding force between the test substances was measured by using the HRP conjugated anti-C1q antibody.

Figure 2:
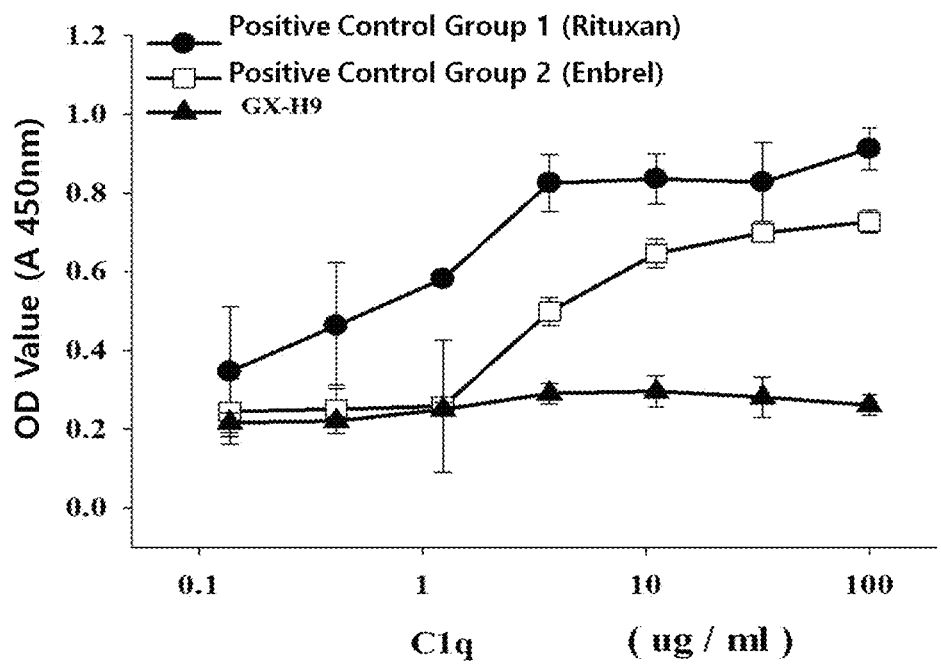
FIG. 2 illustrates a result of binding affinity of C1q for the recombinant hGH (GX-H9)

As a result, it was verified that the GX-H9 had low binding force with the Fcγ receptor I inducing the antibody-dependent cell-mediated cytotoxicity as illustrated in FIG. 1 and low binding force with C1q inducing the complement-mediated cytotoxicity as illustrated in FIG. 2.

Example 3. Preclinical Test Result of Recombinant hGH GX-H9

3-1: Efficacy Test for Subcutaneous Repeated Administration of GX-H9 Using Hypophysectomized Rats Efficacy of GX-H9 was tested by using hypophysectomized rats as an animal disease model. As a control group, Genotropin (Pfizer Corporation, USA) as an daily administration agent was used, and GX-H9 was administered once a week and then efficacy was compared.

A test was performed by targeting a weight gain of 10% or less for about 1 week after hypophysectomization. Group 1 was a negative control group and subcutaneously administered with only a formulation buffer for two weeks. Group 2 was subcutaneously administered with Genotropin by 0.2 mg/kg every day. Group 3 was administered once a week with Genotropin of 1.4 mg/kg which was a weekly dosage. Group was administered once a week with GX-H9 of 1.4 mg/kg (corresponding to a weekly dosage of Genotropin). Group 5 was administered once a week with GX-H9 of 3.5 mg/kg (corresponding to ½ of a molar number of a weekly dosage of Genotropin). Group 6 was administered once a week with GX-H9 of 7.0 mg/kg (corresponding to the same molar number as a weekly dosage of Genotropin). After administration of the drug, symptoms were observed and weights were measured every day.

Figure 3:
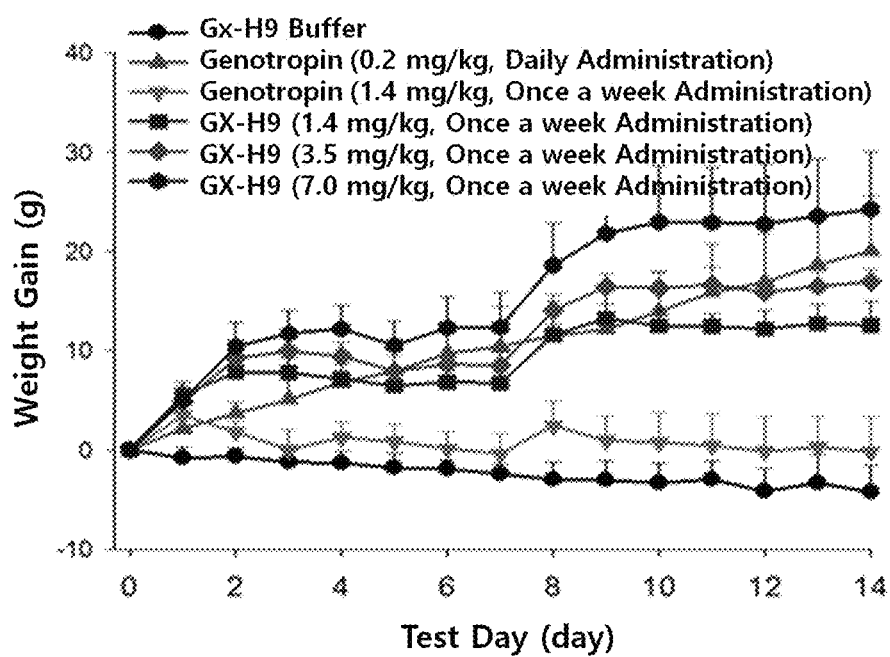
FIG. 3 is a result of the weight gain in hypophysectomized rats.

As a result, as illustrated in FIG. 3, when Genotropin was administered once a day, the weight of average about 20 g/kg was increased when administering 0.2 mg/kg per day, but when a weekly dosage (1.4 mg/kg) was administered all together once a week, there was no weight gain. When the GX-H9 was administered at a dosage of 7 mg/kg once a week (Group 6), the weight gain was greater than that of Genotropin (Group 3) administered with the same mole number. In addition, when the GX-H9 was administered at a dosage of 3.5 mg/kg (group 5), similar efficacy was shown to a case where Genotropin was administered by 0.2 mg/kg daily (Group 2).

3-2: Pharmacodynamics Test after Single Subcutaneous Administration of Recombinant hGH GX-H9 Using Rats To test the pharmacokinetics of GX-H9, GX-H9 was administered to rats once subcutaneously. As a control group, Eutropin (LG Life Sciences, Inc., in Korea) was administered once subcutaneously and efficacy were compared. Group 1 was administered with a single dosage of 200 ug/kg of Eutropin subcutaneously and Group 2 was administered with a single dosage of 200 ug/kg of GX-H9 subcutaneously. Group 3 was administered with a single dosage of 1,000 ug/kg of GX-H9 subcutaneously.

Blood was taken before and for 1, 4, 8, 12, 18, 24, 36, 48, 72, 96, 120, 144, 168, 216, 264 and 336 hours after subcutaneous administration. The blood concentration of each substance was measured by specific bioassay (ELISA).

Figure 4:
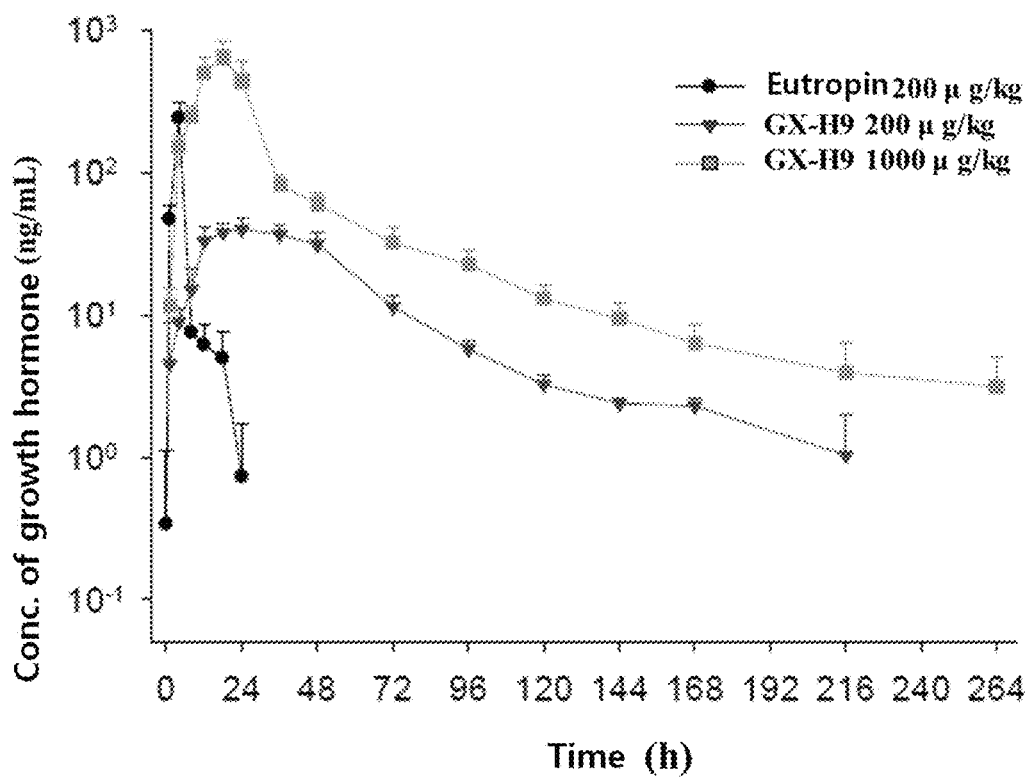
FIG. 4 illustrates characteristics of pharmacodynamics in a single subcutaneous administration of the recombinant hGH (GX-H9) to rats.

The test results were illustrated in FIG. 4 and pharmacokinetics after single subcutaneous administration of GX-H9 at a dosage of 200 or 1,000 ug/kg were reached the highest blood concentration at 17 or 24 hours (Tmax) and the GX-H9 was detected in the blood until 9 days and 11 days. As the dose increased, systemic exposure also increased.

When compared with an administration group of 200 ug/kg of Eutropin as a control substance, a test substance was detected in the blood for a longer time (Eutropin 24 h vs GX-H9 9 day). In the case of subcutaneous administration of 200 ug/kg of GX-H9, the difference of time reaching the maximum blood concentration (Tmax) was about 20 hrs (Eutropin 4 h vs GX-H9 24 h). From the above results, it was observed that GX-H9 was continuously exposed to the system in the rat for a long time as compared with a control drug, Eutropin. In addition, as the dosage of the GX-H9 increased, the systemic exposure after subcutaneous administration proportionally increased.

3-3: Pharmacodynamics Test after Single Subcutaneous Administration of Recombinant hGH GX-H9 in Monkey Pharmacokinetics of GX-H9 and Eutropin as a control substance were analyzed in cynomolgus monkey. In male monkeys (three/group), GX-H9 was subcutaneously administered repeatedly four times a week with dosages of 500 μg/kg and 1000 μg/kg and Eutropin as a control substance was subcutaneously administered once at a dosage of 1000 μg/kg.

In the group administered with GX-H9, blood samples were taken before the 1st and 4th administration (administration of 0 and 21 days) and for 1, 4, 8, 12, 18, 24, 30, 36, 48, 60, 72, 96, 120, 144 and 168 hours after administration.

In a group administered with Eutropin, blood samples were taken before single administration and at 1, 4, 8, 12, 18, 24, 30, 36, 48, 60, 72, 96, 120, 144, and 168 hrs after administration.

Figure 5:
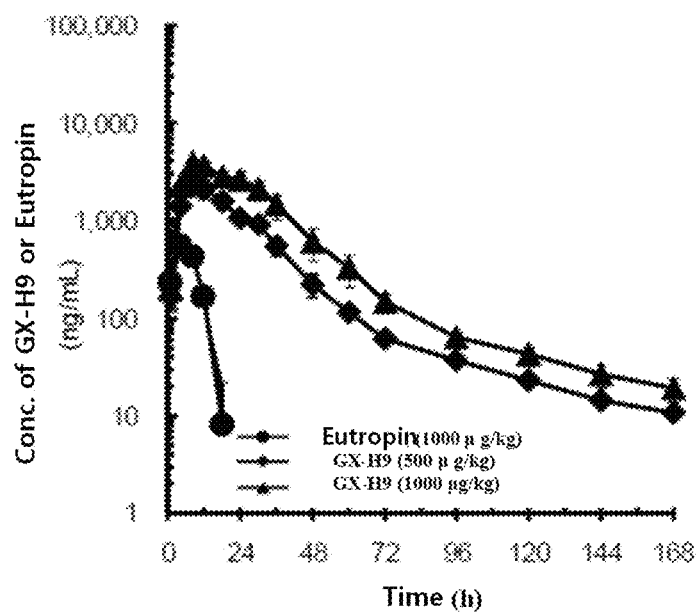
FIG. 5 illustrates the characteristics of pharmacodynamics in a single subcutaneous administration of the recombinant hGH (GX-H9) in monkeys.
Figure 6:
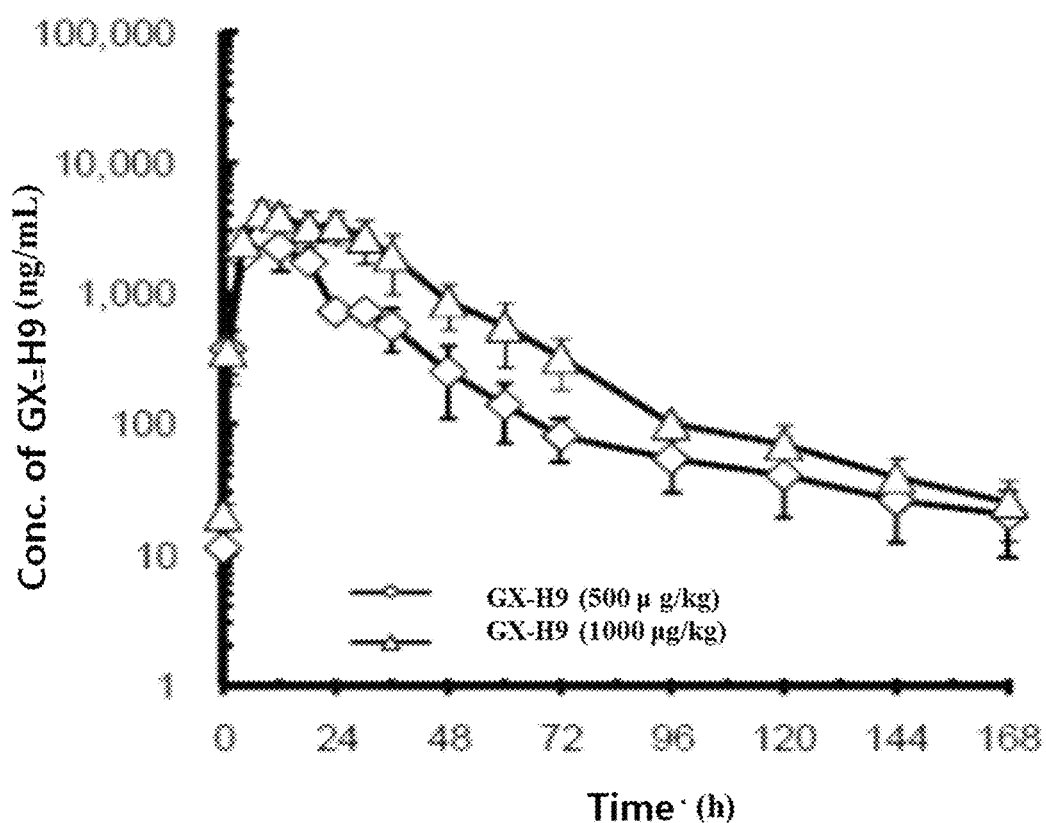
FIG. 6 illustrates the characteristics of pharmacodynamics in a repeated subcutaneous administration of the recombinant hGH (GX-H9) in monkeys.

The blood concentration was measured by specific bioassay (ELISA) for GX-H9 and Eutropin and the results were illustrated in FIGS. 5 and 6. When GX-H9 was subcutaneously administered at a dosage of 500 or 1,000 μg/kg, it was observed that systemic exposure increased in relation to a dose increase after single administration (0 day) and after repeated administration (4 weeks).

As compared with Eutropin (1000 μg/kg, single subcutaneous administration), administration of GX-H9 (500 or 1000 μg/kg) was detected (12 to 18 hrs after administration of Eutropin vs 168 hrs after administration of GX-H9) for a longer time in the blood. That is, when GX-H9 is administered subcutaneously, it was observed that the systemic exposure was more persistent than that of control drug, Eutropin. In addition, as the dosage of GX-H9 increased from 500 to 1000 μg/kg, it was observed that the systemic exposure after subcutaneous administration increased in proportion to the dose increase.

Example 4. Phase 1 Clinical Study Result of Recombinant hGH GX-H9

4-1: Pharmacokinetic Characteristics of Recombinant hGH GX-H9 in Healthy Adults

A Phase 1 clinical study of a randomized, double-blind, placebo-controlled, single ascending dose was performed by targeting healthy volunteers. The purpose of the Phase 1 clinical study was to evaluate safety, tolerability, and pharmacodynamic/pharmacokinetic characteristics after single subcutaneous administration of GX-H9. After healthy volunteers were randomly assigned to a study group or a placebo group, evaluation was performed for a total of 56 days after single subcutaneous administration of GX-H9 to four dosage groups (0.2, 0.4, 0.8 and 1.6 mg/kg).

In the group administered with GX-H9, blood samples were taken before single administration and at 0.25, 1, 2, 4, 6, 8, 12, 16, 24, 28, 32, 36, 40, 48, 54, 60, 72, 80, 96, 144, 312, 480, 648, and 1320 hrs after administration.

Figure 7:
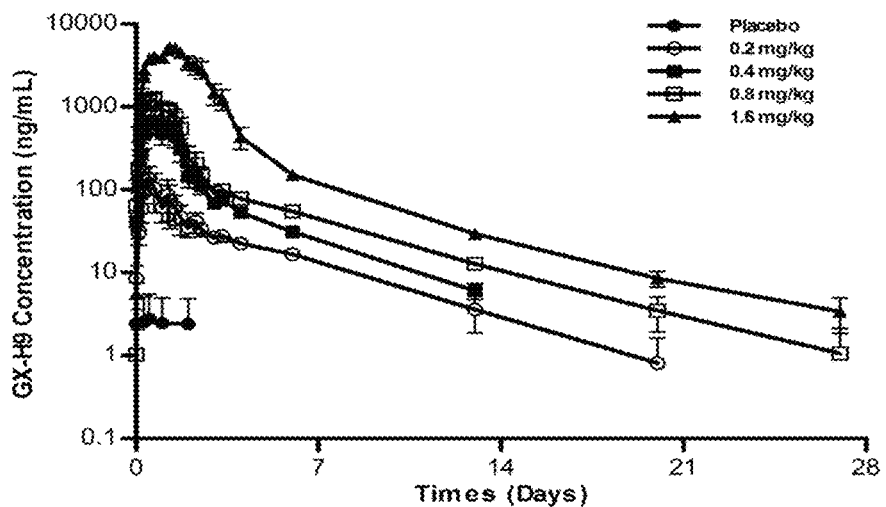
FIG. 7 illustrates the characteristics of pharmacodynamics of the recombinant hGH (GX-H9) in a Phase 1 clinical study.

The blood concentration was measured by the specific bioassay (ELISA) of GX-H9 and the results were illustrated in Table 1 below and FIG. 7.

A peak at a geometric mean concentration was observed at about 12 hours (8 to 16 hours) after single subcutaneous administration of GX-H9, and a second peak at a lower concentration was observed at about 32 hours (28 to 32 hours) after administration. At the maximum dosage, the second peak corresponded to $C_{max}$ (see FIG. 7). $C_{max}$ and AUC were increased more the dosage over all dosages. A half-life ($t_{1/2}$) was from 69.2 hrs to 138 hrs and there was a individual variability.

4-2: Pharmacokinetic Characteristics of Recombinant hGH GX-H9 in Healthy Adults

In the group administered with GX-H9, blood was taken before single administration and the blood was taken at 12, 24, 36, 48, 60, 72, 96, 144, 312, 480, 648 and 1320 hours after administration. A change amount was illustrated in FIG. 8 by setting the concentration of IGF-1 in the blood measured before the administration as a baseline.

Figure 8:
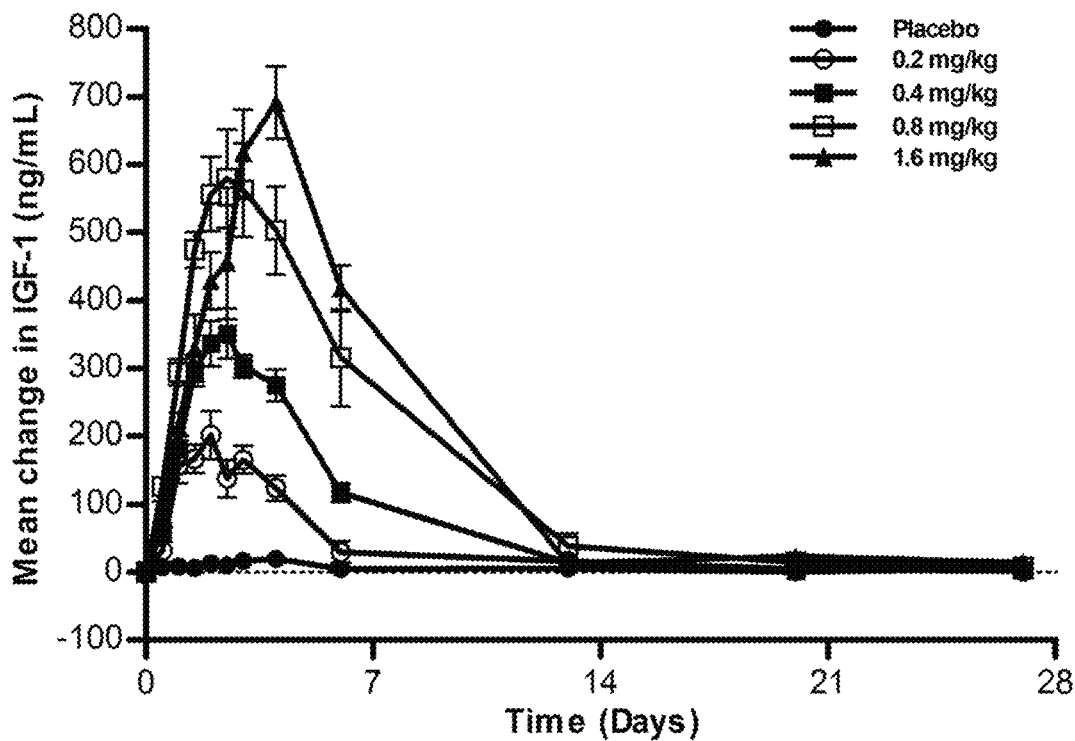
FIG. 8 illustrates the characterisitics of pharmacokinetic (IGF-1 SDS) of the recombinant hGH (GX-H9) in a Phase 1 clinical study.

FIG. 8 illustrates a change amount of the concentration (ng/mL) of IGF-1 in the blood as compared with a baseline of groups administered with placebo and 0.2, 0.4, 0.8 and 1.6 mg/kg of GX-H9. After the single administration of GX-H9 subcutaneously at 0.2, 0.4, 0.8 and 1.6 mg/kg, the concentration of IGF-1 in the blood was increased in proportion to the dosages. The mean maximum increase (% change to baseline) was 81%, 157%, 301% and 349% at the dosage of 0.2, 0.4, 0.8 and 1.6 mg/kg, respectively. The time reaching the highest concentration of IGF-1 in the blood was 48 to 96 hours and was increased in proportion to the dosage. It was verified that the mean concentration of IGF-1 was recovered to the baseline at the 7-th day after administration at the dosage of 0.2 mg/kg and at the 14-th day at other dosages.

4-3: Safety Result of Recombinant hGH GX-H9 in Healthy Adults

Table 2 below summarized the results of treatment emergent adverse events observed in subjects according to the administered drug, relation between the drug and the adverse events, and the intensity of the adverse events.

TABLE 1

| Group | $C_{max}$ | $t_{max}$ | $AUC_{0-t}$ | $AUC_{0-inf}$ | $t_{1/2}$ | CL/F | $V_z/F$ |
| --- | --- | --- | --- | --- | --- | --- | --- |
| 0.2 mg/kg | 105 | 12.00 | 6267 | 8175 | 112 | 1.93 | 312 |
| GX-H9 (N = 6) | (48.7-354) | (8.00-28.00) | (3700-13952) | (5276-15544) | (53.8-200) | (1.07-2.69) | (82.8-739) |
| 0.4 mg/kg | 571 | 14.01 | 26339 | 27350 | 69.2 | 1.09 | 109 |
| GX-H9 (N = 6) | (108-1240) | (8.02-36.00) | (9711-50387) | (10371-51393) | (37.8-86.4) | (0.514-2.77) | (54.1-304) |
| 0.8 mg/kg | 1095 | 16.00 | 45361 | 47286 | 138 | 1.36 | 271 |
| GX-H9 (N = 6) | (364-2300) | (8.00-28.00) | (15432-109352) | (16864-117144) | (79.4-1008) | (0.535-4.36) | (137-778) |
| 1.6 mg/kg | 5100 | 34.00 | 274161 | 327672[#] | 95.7[#] | 0.361[#] | 49.9[#] |
| GX-H9 (N = 6) | (2180-6790) | (16.00-36.05) | (115210-396879) | (253881-398045) | (71.3-143) | (0.285-0.563) | (32.9-58.7) |

$t_{max}$ was evaluated in median (range).

[#]n = 5 (the derived parameter of the value of $t_{1/2}$ from one volunteer was not reliably determined)

TABLE 2

| Group | Severe | | | | | | Moderate | | | | | | Total | | | | | | | | |
|---|---|---|---|---|---|---|---|---|---|---|---|---|---|---|---|---|---|---|---|---|---|
| | Related | | | Unrelated | | | Related | | | Unrelated | | | Related | | | Unrelated | | | Total | | |
| | E | n | (%) | E | n | (%) | E | n | (%) | E | n | (%) | E | n | (%) | E | n | (%) | E | n | (%) |
| Placebo control group (N = 8) | 3 | 3 | (38%) | 6 | 4 | (50%) | | | | | | | 3 | 3 | (38%) | 6 | 4 | (50%) | 9 | 4 | (50%) |
| 0.2 mg/kg GX-H9 (N = 6) | 2 | 1 | (17%) | 5 | 3 | (50%) | | | | | | | 2 | 1 | (17%) | 5 | 3 | (50%) | 7 | 3 | (50%) |
| 0.4 mg/kg GX-H9 (N = 6) | 1 | 1 | (17%) | 7 | 3 | (50%) | | | | | | | 1 | 1 | (17%) | 7 | 3 | (50%) | 8 | 4 | (67%) |
| 0.8 mg/kg GX-H9 (N = 6) | 6 | 4 | (67%) | 4 | 3 | (50%) | | | | | | | 6 | 4 | (67%) | 4 | 3 | (50%) | 10 | 5 | (83%) |
| 1.6 mg/kg GX-H9 (N = 6) | 12 | 5 | (83%) | 7 | 4 | (67%) | | | | 1 | 1 | (17%) | 12 | 5 | (83%) | 8 | 4 | (67%) | 20 | 5 | (83%) |
| Total Active (N = 24) | 21 | 11 | (46%) | 23 | 13 | (54%) | | | | 1 | 1 | (4%) | 21 | 11 | (46%) | 24 | 13 | (54%) | 45 | 17 | (71%) |
| Total (N = 32) | 24 | 14 | (44%) | 29 | 17 | (53%) | | | | 1 | 1 | (3%) | 24 | 14 | (44%) | 30 | 17 | (53%) | 54 | 21 | (66%) |

N = Numebr of individuals exposed to drug
n = Numebr of individuals showing adverse events
E = Numebr of adverse events
(%) = Ratio of individuals experiencing adverse events according to treatment (n/N)*100
Serious adverse events or mild adverse events were not recorded As illustrated in Table 2, a total of 54 adverse events were reported from 21 subjects. No deaths or serious adverse events were reported. An adverse event with severe severity was reported in one subject, but it was determined that it was not an adverse event related to the drug. The severity of all of the adverse events except for the above adverse event was mild. The most frequently reported adverse events were musculoskeletal and connective tissue disorders (19 cases), systemic disorders and administration site disorders (11 cases), and neurological disorders (10 cases). The reported three or more adverse events were myalgia (7 cases), catheter insertion site reaction (6 cases), headache (5 cases), nasopharyngitis (5 cases), arthralgia (4 cases) and melagra (3 cases).

Meanwhile, the formation of antibody of GX-H9 was analyzed in the subject to which GX-H9 was administered. Anti-drug antibody (ADA) was observed before administration, and on 28-th and 56-th day. As a result, no patient showed the antibody formed by GX-H9.

Example 5. Phase 2 Clinical Study Result of Recombinant hGH GX-H9

5-1: Pharmacokinetic Characteristics of GX-H9 in Adult Patients with Growth Hormone Deficiency A Phase 2, randomized, active-controlled, open-label clinical study was conducted to evaluate safety, tolerability, efficacy and pharmacodynamic/pharmacokinetic characteristics of the GX-H9 in adult patients with growth hormone deficiency (Table 3). The dosage was repeatedly administered for a total of 12 weeks with 0.1 mg/kg weekly (Group 1), 0.3 mg/kg twice-monthly (Group 2), or 0.2 mg/kg twice-monthly (Group 3). In addition, as the active control drug, Genotropin was administered daily by 6 μg/kg (G: Group 4).

TABLE 3

| patient no. | group | sex | age |
|---|---|---|---|
| 1 | 1 | M | 32 |
| 2 | 1 | M | 30 |
| 3 | 1 | M | 30 |
| 4 | 1 | M | 27 |
| 5 | 1 | M | 36 |
| 6 | 1 | M | 46 |
| 7 | 1 | F | 60 |
| 8 | 1 | F | 57 |
| 9 | 1 | F | 51 |
| 10 | 1 | M | 49 |
| 11 | 1 | M | 47 |
| 13 | 2 | M | 60 |
| 14 | 2 | M | 26 |
| 15 | 2 | F | 46 |
| 16 | 2 | M | 27 |
| 17 | 2 | F | 22 |
| 18 | 2 | M | 52 |
| 19 | 2 | M | 64 |
| 20 | 2 | M | 31 |
| 21 | 2 | M | 53 |
| 22 | 2 | M | 37 |
| 23 | 2 | M | 55 |
| 24 | 2 | F | 37 |
| 25 | 3 | M | 38 |
| 26 | 3 | F | 31 |
| 27 | 3 | M | 44 |
| 28 | 3 | M | 45 |
| 29 | 3 | F | 31 |
| 30 | 3 | F | 63 |
| 31 | 3 | F | 43 |
| 32 | 3 | M | 47 |
| 33 | 3 | M | 40 |
| 34 | 3 | M | 50 |
| 35 | 3 | M | 51 |
| 36 | 3 | F | 60 |
| 37 | 4 | M | 66 |
| 38 | 4 | F | 29 |
| 39 | 4 | M | 37 |
| 40 | 4 | F | 44 |
| 41 | 4 | M | 35 |
| 42 | 4 | M | 21 |
| 43 | 4 | M | 23 |
| 44 | 4 | M | 27 |
| 45 | 4 | M | 38 |

In the group administered with the GX-H9 once a week, the blood was taken during the first administration (1st week) and the last administration (12th week) and taken at 1, 2, 4, 8, 12, 18, 24, 48, 72 and 168 hrs after administration.

In the group administered with the GX-H9 twice-monthly, the blood was taken before the first administration (first week) and the last administration (11-th week) and taken at 1, 2, 4, 8, 12, 18, 24, 48, 72, 168, 240 and 336 hrs after administration.

Figure 9:
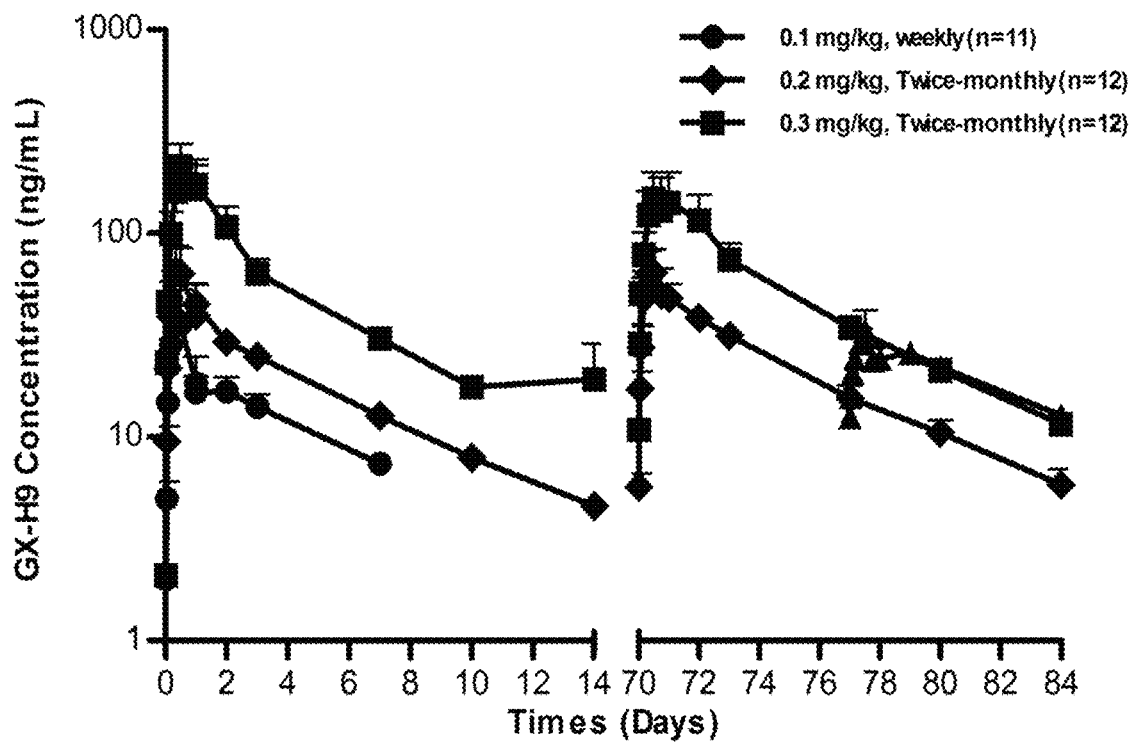
FIG. 9 illustrates the characteristics of pharmacodynamics in a repeated administration of the recombinant hGH (GX-H9) in a Phase 2) clinical study.

The concentration of the GX-H9 in the blood was measured from the obtained blood samples and the results were illustrated in Tables 4 to 6 and FIG. 9.

TABLE 4

| Group 1 (0.1 mg/kg, weekly) | | | | | | |
|---|---|---|---|---|---|---|
| Week | Time | Mean | SD | Median | Min | Max |
| 1 W | Predose | 2.01 | — | 2.01 | 2.01 | 2.01 |
|  | 1 h | 5.01 | 2.94 | 4.23 | 2.36 | 11.53 |
|  | 2 h | 14.87 | 19.28 | 6.59 | 3.43 | 64.25 |
|  | 4 h | 28.34 | 39.78 | 9.24 | 2.88 | 128.35 |
|  | 8 h | 37.83 | 68.95 | 10.24 | 2.29 | 225.02 |
|  | 12 h | 35.63 | 55.05 | 15.67 | 2.20 | 181.13 |
|  | 18 h | 18.32 | 20.17 | 9.45 | 2.70 | 65.81 |
|  | 24 h | 16.58 | 11.04 | 17.05 | 2.17 | 38.92 |
|  | 48 h | 16.70 | 9.81 | 16.79 | 3.34 | 30.33 |
|  | 72 h | 14.09 | 6.95 | 15.97 | 4.37 | 21.80 |
|  | 168 h | 7.41 | 2.71 | 7.34 | 2.49 | 11.76 |
| 12 W | Predose | 12.52 | 2.92 | 12.94 | 8.41 | 17.67 |
|  | 1 h | 15.67 | 4.04 | 15.71 | 9.42 | 23.21 |
|  | 2 h | 20.70 | 8.70 | 21.60 | 10.46 | 35.73 |
|  | 4 h | 24.19 | 10.84 | 22.86 | 10.43 | 44.43 |
|  | 8 h | 28.89 | 17.64 | 24.16 | 10.99 | 73.31 |
|  | 12 h | 33.35 | 28.20 | 25.39 | 10.98 | 110.06 |
|  | 18 h | 23.74 | 12.27 | 21.72 | 9.00 | 50.42 |
|  | 24 h | 24.17 | 14.01 | 21.65 | 11.26 | 61.57 |
|  | 48 h | 26.00 | 9.55 | 27.44 | 12.65 | 38.46 |
|  | 72 h | 22.01 | 6.97 | 23.64 | 14.43 | 32.37 |
|  | 168 h | 12.75 | 4.92 | 11.77 | 5.73 | 21.28 |

TABLE 5

| Group 2 (0.3 mg/kg, Twice-monthly) | | | | | | |
|---|---|---|---|---|---|---|
| Week | Time | Mean | SD | Median | Min | Max |
| 1 W | Predose | 2.10 | — | 2.10 | 2.10 | 2.10 |
|  | 1 h | 23.20 | 23.56 | 13.06 | 2.70 | 74.68 |
|  | 2 h | 46.14 | 40.78 | 29.60 | 3.52 | 119.32 |
|  | 4 h | 99.49 | 96.99 | 65.22 | 12.26 | 312.01 |
|  | 8 h | 160.53 | 179.70 | 107.49 | 13.94 | 641.98 |
|  | 12 h | 213.21 | 214.23 | 168.64 | 11.86 | 699.11 |
|  | 18 h | 165.87 | 172.00 | 93.14 | 11.15 | 445.85 |
|  | 24 h | 173.54 | 194.85 | 121.49 | 13.91 | 597.79 |
|  | 48 h | 107.71 | 95.65 | 65.66 | 22.32 | 290.37 |
|  | 72 h | 63.70 | 37.71 | 49.99 | 19.35 | 128.65 |
|  | 168 h | 30.43 | 14.64 | 24.79 | 14.33 | 59.71 |
|  | 240 h | 17.67 | 7.40 | 15.58 | 11.30 | 36.05 |
|  | 336 h | 19.20 | 31.66 | 9.86 | 5.21 | 113.69 |
| 11 W | Predose | 10.89 | 4.10 | 10.40 | 4.72 | 17.75 |
|  | 1 h | 28.72 | 24.53 | 17.34 | 8.37 | 84.15 |
|  | 2 h | 53.91 | 50.49 | 34.38 | 11.19 | 151.94 |
|  | 4 h | 78.89 | 76.77 | 52.08 | 13.69 | 258.54 |
|  | 8 h | 132.65 | 135.54 | 62.56 | 22.65 | 435.16 |
|  | 12 h | 148.42 | 174.84 | 58.52 | 17.01 | 580.24 |
|  | 18 h | 130.20 | 199.98 | 54.56 | 15.46 | 730.83 |
|  | 24 h | 141.26 | 198.15 | 69.33 | 20.28 | 738.26 |
|  | 48 h | 115.82 | 135.33 | 64.10 | 21.43 | 481.25 |
|  | 72 h | 74.40 | 52.33 | 56.64 | 21.19 | 197.28 |
|  | 168 h | 34.64 | 13.79 | 32.26 | 20.53 | 71.03 |
|  | 240 h | 21.37 | 8.64 | 19.24 | 10.70 | 39.98 |
|  | 336 h | 11.58 | 4.70 | 11.07 | 4.51 | 20.63 |

TABLE 6

| Group 3 (0.2 mg/kg, Twice-monthly) | | | | | | |
|---|---|---|---|---|---|---|
| Week | Time | Mean | SD | Median | Min | Max |
| 1 W | Predose | — | — | — | — | — |
|  | 1 h | 10.64 | 6.35 | 9.09 | 3.35 | 21.51 |
|  | 2 h | 23.93 | 19.02 | 24.79 | 4.69 | 56.43 |
|  | 4 h | 37.89 | 33.96 | 37.37 | 5.24 | 85.93 |
|  | 8 h | 67.01 | 81.94 | 28.71 | 10.92 | 236.12 |
|  | 12 h | 67.17 | 83.37 | 28.02 | 12.76 | 245.62 |
|  | 18 h | 47.21 | 69.50 | 18.22 | 7.01 | 213.04 |
|  | 24 h | 50.89 | 46.57 | 38.16 | 21.58 | 170.68 |
|  | 48 h | 29.31 | 8.40 | 29.18 | 17.83 | 41.02 |
|  | 72 h | 23.56 | 5.48 | 23.25 | 12.08 | 30.71 |
|  | 168 h | 10.98 | 3.62 | 11.42 | 4.23 | 15.71 |
|  | 240 h | 7.16 | 2.44 | 7.95 | 3.84 | 10.23 |
|  | 336 h | 4.57 | 1.07 | 4.54 | 3.52 | 5.66 |
| 11 W | Predose | 3.45 | 1.05 | 3.03 | 2.75 | 4.99 |
|  | 1 h | 22.99 | 16.71 | 19.90 | 8.98 | 43.17 |
|  | 2 h | 18.71 | 8.94 | 17.37 | 10.52 | 28.24 |
|  | 4 h | 61.84 | 74.97 | 30.99 | 13.04 | 172.34 |
|  | 8 h | 24.89 | 15.48 | 18.51 | 13.63 | 42.54 |
|  | 12 h | 84.46 | 106.13 | 42.95 | 11.73 | 240.19 |
|  | 18 h | 72.53 | 95.15 | 32.42 | 12.23 | 213.05 |
|  | 24 h | 57.04 | 47.03 | 44.36 | 15.52 | 123.94 |
|  | 48 h | 35.16 | 3.07 | 36.47 | 31.65 | 37.35 |
|  | 72 h | 28.70 | 3.88 | 27.51 | 25.46 | 34.32 |
|  | 168 h | 13.53 | 3.14 | 13.28 | 10.52 | 16.79 |
|  | 240 h | 6.77 | 1.73 | 6.42 | 5.24 | 8.65 |
|  | 336 h | 3.70 | 0.97 | 3.53 | 2.81 | 4.92 |

After repeated administration of the GX-H9 with 0.1 mg/kg for 12 weeks, the change in pharmacokinetics was analyzed at the first administration (1st week) and the last administration (12th week), before administration, and 1, 2, 4, 8, 12, 18, 24, 48, 72 and 168 hrs after administration. It was verified that the mean (standard deviation) concentration of GX-H9 from before administration (below limit of quantitation, BLQ) until 168 hrs (7 days) after the administration for first (1st week) and the last administration (12th week) were 7.41 (2.71) and 12.75 (4.92), respectively. Further, after repeated administration of the GX-H9 with 0.3 mg/kg and 0.2 mg/kg for 12 weeks, the change in pharmacokinetics was analyzed at the first administration (1st week) and the last administration (11th week), before administration, and 1, 2, 4, 8, 12, 18, 24, 48, 72, 168, 240 and 336 hrs after administration. It was verified that the mean (standard deviation) concentration of GX-H9 from before administration (below limit of quantitation, BLQ) until 336 hrs (14 days) after the administration for first (1st week) and the last administration (12th week) were 19.20 (31.66) and 11.58 (4.70) for 0.3 mg/kg/twice-monthly interval and 4.57 (1.07) and 3.70 (0.97) for 0.2 mg/kg/twice-monthly, respectively.

Therefore, it was shown that when GX-H9 was administered weekly or twice-monthly in the concentration range of 0.1 mg/kg to 0.3 mg/kg, the concentration of GX-H9 was maintained at a normal level while without any accumulation in the body.

5-2: Pharmacokinetic Characteristics of Recombinant hGH GX-H9 in Adult Patients with Growth Hormone Deficiency In a group administered with GX-H9 once a week, the blood was taken during the first administration (1st week) and the last administration (12th weeks) and taken at 12, 24, 48, 72 and 168 hrs after administration. In order to evaluate a change in IGF-1 standard deviation score (IGF-1 SDS) compared to the normal person in relation to time and dose strength, the IGF-1 SDS was analyzed at 4 days after administration of 3, 5, 7, 9, and 11-th weeks. In the group administered with GX-H9 twice-monthly, the blood was taken during the first administration (1st week) and the last administration (11th weeks) and taken at 12, 24, 48, 72, 168, 240 and 336 hrs after administration. In order to evaluate a change in IGF-1 SDS in relation to time and dose strength, the change of IGF-1 SDS was analyzed at 4 days after administration of 3, 5, 7, and 9-th weeks.

Figure 10:
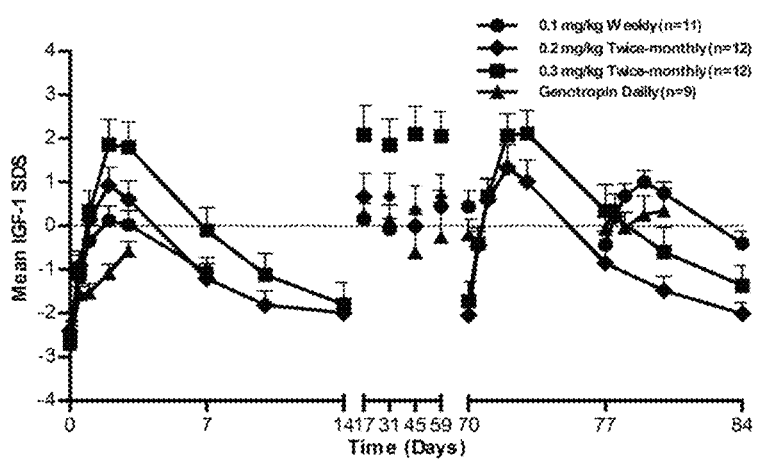
FIG. 10 illustrates the characteristics of pharmacokinetic in a repeated administration of the recombinant hGH (GX-H9) in a Phase 2 clinical study.

The results of characteristics of pharmacodynamics of GX-H9 were illustrated in Tables 7 to 10 and FIG. 10.

TABLEs 7

| | | Group 1 (0.1 mg/kg, weekly) | | | | |
|---|---|---|---|---|---|---|
| Week | Time | Mean | SD | Median | Min | Max |
| 1 W | Predose | −2.48 | 0.93 | −2.37 | −4.07 | −1.49 |
| | 12 h | −1.18 | 1.00 | −1.11 | −2.84 | 0.71 |
| | 24 h | −0.35 | 1.22 | −0.56 | −2.12 | 2.23 |
| | 48 h | 0.12 | 1.10 | −0.15 | −1.58 | 2.51 |
| | 72 h | 0.03 | 1.07 | −0.02 | −2.08 | 2.20 |
| | 168 h | −1.05 | 1.10 | −0.79 | −3.23 | 0.53 |
| 3 W | | 0.16 | 1.17 | 0.28 | −2.57 | 2.22 |
| 5 w | | −0.07 | 0.80 | 0.01 | −1.80 | 0.94 |
| 7 W | | −0.01 | 0.91 | 0.08 | −1.48 | 1.29 |
| 9 W | | 0.44 | 1.23 | 0.68 | −2.44 | 1.66 |
| 11 W | | 0.44 | 1.20 | 0.66 | −1.20 | 2.14 |
| 12 W | Predose | −0.43 | 1.02 | −0.45 | −2.27 | 0.95 |
| | 12 h | 0.21 | 0.90 | 0.08 | −1.42 | 1.88 |
| | 24 h | 0.69 | 0.93 | 0.73 | −0.87 | 2.60 |
| | 48 h | 1.01 | 0.87 | 0.95 | −0.52 | 2.39 |
| | 72 h | 0.75 | 0.84 | 0.73 | −1.09 | 1.91 |
| | 168 h | −0.41 | 0.97 | −0.42 | −2.27 | 1.15 |

TABLE 8

| | | Group 2 (0.3 mg/kg, Twice-monthly) | | | | |
|---|---|---|---|---|---|---|
| Week | Time | Mean | SD | Median | Min | Max |
| 1 W | Predose | −2.64 | 1.25 | −2.32 | −5.42 | −1.29 |
| | 12 h | −0.97 | 1.34 | −0.67 | −4.21 | 0.70 |
| | 24 h | 0.30 | 1.73 | 0.15 | −2.99 | 3.30 |
| | 48 h | 1.86 | 2.00 | 1.79 | −1.20 | 5.20 |
| | 72 h | 1.80 | 1.99 | 1.71 | −1.33 | 4.85 |
| | 168 h | −0.10 | 1.79 | 0.60 | −4.14 | 2.34 |
| | 240 h | −1.12 | 1.68 | −0.56 | −4.81 | 1.32 |
| | 336 h | −1.79 | 1.67 | −2.01 | −5.39 | 0.34 |
| 3 W | | 2.09 | 2.32 | 2.02 | −2.28 | 5.91 |
| 5 W | | 1.85 | 2.05 | 1.91 | −1.44 | 5.55 |
| 7 W | | 2.10 | 2.20 | 2.34 | −1.20 | 6.52 |
| 9 W | | 2.06 | 1.93 | 2.64 | −0.96 | 4.34 |
| 11 W | Predose | −1.72 | 1.53 | −1.77 | −4.92 | 0.86 |
| | 12 h | −0.40 | 1.27 | −0.12 | −3.18 | 1.20 |
| | 24 h | 0.68 | 1.43 | 1.02 | −1.96 | 2.73 |
| | 48 h | 2.07 | 1.71 | 1.51 | −0.31 | 5.14 |
| | 72 h | 2.12 | 1.82 | 1.88 | −0.43 | 5.16 |
| | 168 h | 0.35 | 2.05 | 0.42 | −3.60 | 3.77 |
| | 240 h | −0.59 | 1.97 | −0.63 | −4.24 | 2.44 |
| | 336 h | −1.36 | 1.59 | −1.56 | −4.44 | 0.82 |

TABLE 9

| | | Group 3 (0.2 mg/kg, Twice-monthly) | | | | |
|---|---|---|---|---|---|---|
| Week | Time | Mean | SD | Median | Min | Max |
| 1 W | Predose | −2.40 | 0.82 | −2.41 | −3.60 | −0.84 |
| | 12 h | −0.92 | 0.84 | −1.11 | −2.72 | 0.66 |
| | 24 h | 0.13 | 1.20 | 0.15 | −2.34 | 2.05 |
| | 48 h | 0.93 | 1.43 | 0.94 | −1.94 | 3.08 |
| | 72 h | 0.61 | 1.44 | 0.95 | −2.45 | 3.10 |
| | 168 h | −1.20 | 1.18 | −1.17 | −3.60 | 0.94 |
| | 240 h | −1.81 | 1.06 | −1.52 | −3.92 | −0.07 |
| | 336 h | −1.99 | 0.93 | −1.99 | −3.76 | −0.58 |
| 3 W | | 0.65 | 1.89 | 1.40 | −3.76 | 2.69 |
| 5 W | | 0.67 | 1.83 | 1.21 | −3.27 | 3.08 |
| 7 W | | 0.35 | 1.97 | 0.79 | −3.04 | 3.02 |
| 9 W | | 0.67 | 1.74 | 1.22 | −2.64 | 2.90 |

TABLE 9-continued

| | | Group 3 (0.2 mg/kg, Twice-monthly) | | | | |
|---|---|---|---|---|---|---|
| Week | Time | Mean | SD | Median | Min | Max |
| 11 W | Predose | −2.04 | 0.95 | −1.91 | −3.70 | −0.49 |
| | 12 h | −0.45 | 1.16 | −0.26 | −3.04 | 1.13 |
| | 24 h | 0.61 | 1.60 | 0.68 | −2.38 | 2.58 |
| | 48 h | 1.33 | 1.83 | 1.14 | −2.20 | 3.99 |
| | 72 h | 1.01 | 1.74 | 1.18 | −2.53 | 3.24 |
| | 168 h | −0.86 | 1.46 | −0.96 | −3.70 | 1.39 |
| | 240 h | −1.47 | 1.11 | −1.53 | −3.65 | 0.34 |
| | 336 h | −2.01 | 0.88 | −1.81 | −3.50 | −0.61 |

TABLE 10

| | | Group 4 (Genotropin 6 μg/kg, daily) | | | | |
|---|---|---|---|---|---|---|
| Week | Time | Mean | SD | Median | Min | Max |
| 1 W | Predose | −2.70 | 0.88 | −2.54 | −4.10 | −1.72 |
| | 12 h | −1.56 | 0.55 | −1.45 | −2.49 | −0.77 |
| | 24 h | −1.52 | 0.61 | −1.58 | −2.39 | −0.55 |
| | 48 h | −1.08 | 0.63 | −1.29 | −2.03 | −0.20 |
| | 72 h | −0.56 | 0.63 | −0.36 | −1.74 | 0.24 |
| 3 W | | 0.29 | 1.04 | 0.24 | −1.66 | 1.60 |
| 5 W | | 0.14 | 0.92 | 0.20 | −1.57 | 1.47 |
| 7 W | | −0.59 | 1.65 | −0.24 | −3.84 | 1.06 |
| 9 W | | −0.24 | 2.04 | 0.45 | −4.26 | 2.20 |
| 11 W | | −0.18 | 0.89 | 0.19 | −1.70 | 0.58 |
| 12 W | Predose | −0.06 | 0.74 | 0.01 | −1.33 | 0.82 |
| | 12 h | 0.42 | 0.82 | 0.63 | −1.15 | 1.25 |
| | 24 h | −0.04 | 0.91 | −0.15 | −1.60 | 1.08 |
| | 48 h | 0.25 | 1.13 | 0.43 | −1.87 | 1.62 |
| | 72 h | 0.35 | 1.36 | 0.60 | −1.62 | 2.03 |

After repeated administration of GX-H9 with 0.1 mg/kg for 12 weeks, the change in pharmacodynamics was analyzed at the first administration (1st week) and the last administration (12th week), before administration, and 12, 24, 48, 72 and 168 hrs after administration. In the patients with growth hormone deficiency, the mean (standard deviation) IGF-1 SDS of −2.48 (0.93) before administration showed change minimum of −0.41 (0.97) and maximum of 1.01 (0.87) within 7 days after during the last administration (12th week). Further, after repeated administration of GX-H9 with 0.3 mg/kg and 0.2 mg/kg for 12 weeks, the change in pharmacodynamics was analyzed at the first administration (1st week) and the last administration (11th week), before administration, and 12, 24, 48, 72, 168, 240 and 336 hrs after administration. In the patients with growth hormone deficiency, the mean (standard deviation) IGF-1 SDS of −2.64 (1.25) and −2.40 (0.82) before administration showed change with minimum of −1.36 (1.59) and −2.01 (0.88) and maximum of 2.12 (1.82) and 1.33 (1.83) within 14 days after the last administration (11th week). Further, after repeated administration of Genotropin, an active control drug, by 6 μg/kg daily, the change in pharmacodynamics was analyzed at the first administration (1st week) and the last administration (12th week), before administration, and 12, 24, 48 and 72 hrs after administration. In patients with growth hormone deficiency, the mean (standard deviation) IGF-1 SDS of −2.70 (0.88) before administration showed change with minimum of and maximum of 0.42 (0.82) within 3 days after the last administration (12th week).

The maximum mean change in IGF-1 SDS of GX-H9 was shown between 48 hours to 72 hours after administration of 0.1 mg/kg at weekly interval or 0.3 mg/kg at a twice-monthly interval and the minimum mean change was shown within 168 to 336 hrs after administration. Meanwhile, Genotropin, an active control drug, which was administered daily, the maximum mean change was shown within 12 hrs after administration and the minimum mean change was reached within 24 hrs after administration.

The goal of treatment for adult patients with growth hormone deficiency is to improve metabolism normalization and quality of life. As it is different according to age and gender of the patients, the IGF-1 level in the blood after administration of GX-H9 needs to be optimized to the middle (50th percentile or 0 SDS) to 1 SDS range within the normal range (−2 SDS to 2 SDS). Accordingly, in the case of administering GX-H9 once a week, it was verified that the range of IGF-1 SDS of the treated patient may be maintained in the normal level by adjusting the treatment dosage in a concentration range of 0.1 mg/kg to 0.2 mg/kg according to IGF-1 level. Further, in the case of administering GX-H9 twice-monthly, it was verified that the range of IGF-1 SDS of the treated patient may be maintained in the normal level by adjusting the treatment dosage in a concentration range of 0.2 mg/kg to 0.4 mg/kg according to IGF-1 level.

5-3: Safety Result of Recombinant hGH GX-H9 in Patients with Growth Hormone Deficiency Results of analyzing adverse events observed in subjects according to the administered drug and relation between the drug and the adverse events were summarized in

TABLE 11

| | Daily Administration | | | | | | | |
|---|---|---|---|---|---|---|---|---|
| | Once a Week 0.1 mg/kg GX-H9 (N11 = 11) | | | 6 µg/kg Genotropin ® (N = 3) | | | Total (N = 14) | |
| | E | n | (%) | E | n | (%) | E | n | (%) |
| Severity Relation to Drug | 11 | 5 | (45.5%) | 2 | 2 | (66.7%) | 13 | 7 | (50.0%) |
| Unrelated | 8 | 4 | (36.4%) | 2 | 2 | (66.7%) | 10 | 6 | (42.9%) |
| Related | 3 | 1 | (9.1%) | 0 | 0 | 0 | 3 | 1 | (7.1%) |

N = Numebr of individuals exposed to drug
n = Numebr of individuals showing adverse events
E = Numebr of adverse events
(%) = Ratio of individuals experiencing adverse events according to treatment (n/N)*100
Serious adverse events or mild adverse events were not observed A total of 11 adverse events were reported in 5 patients administered with GX-H9 once a week. No deaths or serious adverse events were reported. The severity of all of the adverse events was mild. The most frequently reported adverse events were 2 cases of musculoskeletal and connective tissue disorders and 3 cases of blood and lymphatic organ disorders. It was reported that 3 adverse events were drug related. All of the reported adverse events were were commonly observed in the conventional growth hormone treatment.

5-4: Antibody Reaction (ADA) Result of Recombinant hGH GX-H9 in Patients with Growth Hormone Deficiency In order to verify the pharmacological effect by continuous administration, it was examined whether antibody formation was induced by GX-H9. In the case of one patient (sample 1502-001), it was shown that the test result was positive because the antibody was present before the start of the clinical trials. Further, there was no increase in value by the GX-H9 even on days 1, 32, and 106-th days after administration. In addition, as a result of examining the pharmacodynamics of the patients, it was verified that the IGF-1 levels were greatly increased, and thus it is suggested that existing anti-hGH antibodies are not associated with GX-H9 therapy. As a result, administration of GX-H9 did not induce antibody responses in the whole patients.

TABLE 12

| Sample | Screening[1] | Specificity[2] | Titer[3] |
|---|---|---|---|
| 1501-001 Test Day 1/Week 1 | <20 | NA | NA |
| 1501-001 Week 5/Test Day 32 | <20 | NA | NA |
| 1501-001 Follow up visit | <20 | NA | NA |
| 1501-003 Test Day 1/Week 1 | <20 | NA | NA |
| 1501-003 Week 5/Test Day 32 | <20 | NA | NA |
| 1501-003 Follow up visit | <20 | NA | NA |
| 1502-001 Test Day 1/Week 1 | Reactive | 63% | 100 |
| 1502-001 Week 5/Test Day 32 | Reactive | 60% | 100 |
| 1502-001 Follow up visit | Reactive | 70% | 100 |
| 1502-002 Test Day 1/Week 1 | <20 | NA | NA |
| 1502-002 Week 5/Test Day 32 | <20 | NA | NA |
| 1502-002 Follow up visit | <20 | NA | NA |
| 1502-004 Test Day 1/Week 1 | <20 | NA | NA |
| 1502-004 Week 5/Test Day 32 | <20 | NA | NA |
| 1502-004 Test Day 1/Week 1 | <20 | NA | NA |
| 1502-006 Test Day 1/Week 1 | <20 | NA | NA |
| 1502-006 Week 5/Test Day 32 | <20 | NA | NA |
| 1503-001 Test Day 1/Week 1 | <20 | NA | NA |
| 1503-001 Week 5/Test Day 32 | <20 | NA | NA |
| 1503-001 Follow up visit | <20 | NA | NA |
| 1503-003 Test Day 1/Week 1 | <20 | NA | NA |
| 1503-003 Week 5/Test Day 32 | <20 | NA | NA |
| 1503-003 Follow up visit | <20 | NA | NA |
| 1503-004 Test Day 1/Week 1 | <20 | NA | NA |
| 1503-004 Week 5/Test Day 32 | <20 | NA | NA |
| 1505-002 Test Day 1/Week 1 | <20 | NA | NA |
| 1505-002 Week 5/Test Day 32 | <20 | NA | NA |
| 1505-002 Follow up visit | <20 | NA | NA |
| 1506-002 Test Day 1/Week 1 | <20 | NA | NA |
| 1506-002 Week 5/Test Day 32 | <20 | NA | NA |

[1]Screening: If sample is non-reactive it will be reported as <20; if reactive, specificity will be assessed
[2]Specificity: % inhibition is defined as 100 × (1 − (mean OD GX-H9 spiked/mean OD unspiked sample)); if ≥17% inhibition sample will be assessed for titer3) Titer value: titer sample is defined as the reciprocal of the dilution that generates a mean OD greater than or equal to the cutpoint OD of the plate where the subsequent dilutions in the series results in a mean OD less than the cutpoint OD
NA: sample non-reactive, additional analysis not required It was known that the recommended dosage of first-generation (daily administration) hGH for treatment of adult growth hormone deficiency was 6 to 12 µg/kg. A dosage of GX-H9 formulation is 0.21 to 0.42 mg/kg once a week and 0.42 to 0.84 mg/kg twice-monthly when being converted into the same molar number as the 7-day amount of the first-generation hGH. However, it was shown that effective dosages verified clinically were different from those predicted by simple calculations. From the result based from simulation and modeling of the pharmacokinetic and pharmacodynamics of the actual clinical trials, it was predicted that the optimal dosage for adult patients with growth hormone deficiency was 0.1 mg/kg to 0.2 mg/kg once a week or 0.2 mg/kg to 0.4 mg/kg twice-monthly. That is, it was observed that the effective dosage for GX-H9 was lower than the dosage predicted from the existing daily hGH amount.

Further, it was verified that when 0.1 mg/kg of the dosage was administered to adult patients once a week for 12 weeks, there were no significant adverse events and there was no antibody response by drug administration. As the result of administering the dosage of 0.3 mg/kg twice-monthly, it was verified that there were no adverse events or antibody response. Therefore, the GX-H9 showed the equivalent efficacy as the growth hormone in the body or the first-generation growth hormone product and had an enhanced half-life, and thus convenience of medication was very improved and safety was verified.

Although the specific part of the present disclosure has been described in detail, it is obvious to those skilled in the art that such a specific description is just a preferred embodiment and the scope of the present disclosure is not limited. Thus, the substantial scope of the present disclosure will be defined by the appended claims and equivalents thereof.

What is claimed is:

1. A method for treating growth hormone deficiency in a human patient in need thereof, comprising
   (i) administering a recombinant human growth hormone (hGH) GX-H9 to the human patient once a week at a dosage of 0.1 to 0.3 mg per weight kg of the human patient, or
   (ii) administering a recombinant hGH GX-H9 to the patient twice a month at a dosage of 0.1 to 0.4 mg per weight kg of the human patient,
   wherein the human patient is an adult, and
   wherein the recombinant hGH GX-H9 comprises the amino acid sequence of SEQ ID NO: 1.

2. The method according to claim 1, wherein the dosage of (i) administering the recombinant hGH GX-H9 once a week is 0.1 to 0.2 mg per weight kg of the human patient.

3. The method according to claim 1, wherein the dosage of (ii) administering the recombinant hGH GX-H9 twice a month is 0.15 to 0.4 mg per weight kg of the human patient.

4. The method according to claim 1, wherein the administering (i) and (ii) are each carried out subcutaneously.

* * * * *